(12) United States Patent
Watanabe et al.

(10) Patent No.: US 10,676,441 B2
(45) Date of Patent: Jun. 9, 2020

(54) METHOD FOR PRODUCING PITAVASTATIN CALCIUM

(71) Applicant: API CORPORATION, Tokyo (JP)

(72) Inventors: Naoyuki Watanabe, Fukuoka (JP); Takanobu Iura, Kanagawa (JP); Hideki Oomiya, Fukuoka (JP); Masaki Nagahama, Fukuoka (JP)

(73) Assignee: API CORPORATION, Tokyo (JP)

( * ) Notice: Subject to any disclaimer, the term of this patent is extended or adjusted under 35 U.S.C. 154(b) by 0 days.

(21) Appl. No.: 15/749,377

(22) PCT Filed: Aug. 5, 2016

(86) PCT No.: PCT/JP2016/073056
§ 371 (c)(1),
(2) Date: Jan. 31, 2018

(87) PCT Pub. No.: WO2017/022846
PCT Pub. Date: Feb. 9, 2017

(65) Prior Publication Data
US 2018/0222865 A1  Aug. 9, 2018

(30) Foreign Application Priority Data
Aug. 5, 2015  (JP) .................. 2015-154864

(51) Int. Cl.
*A61K 31/47*   (2006.01)
*C12P 17/12*   (2006.01)
(Continued)

(52) U.S. Cl.
CPC ............ *C07D 215/14* (2013.01); *C12P 17/12* (2013.01); *A61K 31/47* (2013.01); *C07B 61/00* (2013.01)

(58) Field of Classification Search
CPC ......... A61K 31/47; C12P 17/12; C07B 61/00; C07D 215/14
See application file for complete search history.

(56) References Cited

U.S. PATENT DOCUMENTS 5,011,930 A    4/1991   Fujikawa et al.
6,437,135 B1   8/2002   Matsumoto et al.
(Continued)

FOREIGN PATENT DOCUMENTS

JP    01-279866    11/1989
JP    05-310700    11/1993
(Continued)

OTHER PUBLICATIONS

International Search Report issued in PCT/JP2016/073056, dated Oct. 25, 2016.
(Continued)

*Primary Examiner* — Sun Jae Yoo
(74) *Attorney, Agent, or Firm* — Greenblum & Bernstein, P.L.C.

(57) ABSTRACT

Production of pitavastatin calcium safely on an industrial scale with a high yield and high selectivity at low cost. A method of producing pitavastatin calcium including step (i) for acetalizing a compound represented by the formula (1) to give a compound represented by the formula (3), step (ii) for reacting a compound represented by the formula (3) with an acid to give a compound represented by the formula (4), and step (iii) for hydrolyzing a compound represented by the formula (4) and reacting same with a calcium compound.

(Continued)

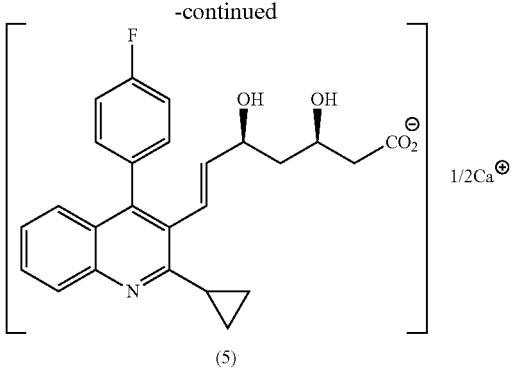

(5)

4 Claims, 1 Drawing Sheet

Specification includes a Sequence Listing.

(51) Int. Cl.
*C07B 61/00* (2006.01)
*C07D 215/14* (2006.01)

(56) References Cited

U.S. PATENT DOCUMENTS

| | | |
|---|---|---|
| 2004/0030139 A1 | 2/2004 | Hara et al. |
| 2005/0048633 A1 | 3/2005 | Hiraoka et al. |
| 2008/0248539 A1 | 10/2008 | Giver et al. |
| 2016/0185734 A1 | 6/2016 | Tateyama et al. |

FOREIGN PATENT DOCUMENTS

| | | |
|---|---|---|
| JP | 2002-300897 | 10/2002 |
| JP | 2002-322153 | 11/2002 |
| JP | 2002-544207 | 12/2002 |
| JP | 2003-137870 | 5/2003 |
| JP | 2003-339387 | 12/2003 |
| JP | 2005-500382 | 1/2005 |
| JP | 2005-34025 | 2/2005 |
| JP | 2005-082591 | 3/2005 |
| JP | 2005-516064 | 6/2005 |
| JP | 2009-24008 | 2/2009 |
| JP | 4270918 | 3/2009 |
| JP | 2009-516728 | 4/2009 |
| JP | 2014-001176 | 1/2014 |
| JP | 2014-533519 | 12/2014 |
| WO | 95/11898 | 5/1995 |
| WO | 00/42016 | 7/2000 |
| WO | 00/68221 | 11/2000 |
| WO | 03/016317 | 2/2003 |
| WO | 03/064382 | 8/2003 |
| WO | 03/078634 | 9/2003 |
| WO | 2006/131933 | 12/2006 |
| WO | 2007/057703 | 5/2007 |
| WO | 2012/032035 | 3/2012 |
| WO | 2012/140490 | 10/2012 |
| WO | 2013/080219 | 6/2013 |
| WO | 2015/030001 | 3/2015 |
| WO | 2015/030002 | 3/2015 |

OTHER PUBLICATIONS

Written Opinion of the ISA issued in PCT/JP2016/073056, dated Oct. 25, 2016.
Yuste et al., "A Simple Method to Prepare Alkyl 3, 5-Dioxohexanoates", *Synthetic Communications* 18(7), 735-739 (1988).
Molecular Cloning: A Laboratory Manual, $2^{nd}$ Ed., Cold Spring Harbor Laboratory, Cold Spring Harbor, NY, pp. 1.90 to 1.105, B.12-B.13 (1989).
English translation of Notice of Reasons for Refusal, Japanese Patent Office, Application No. 2017-533133, dated Jul. 12, 2019.

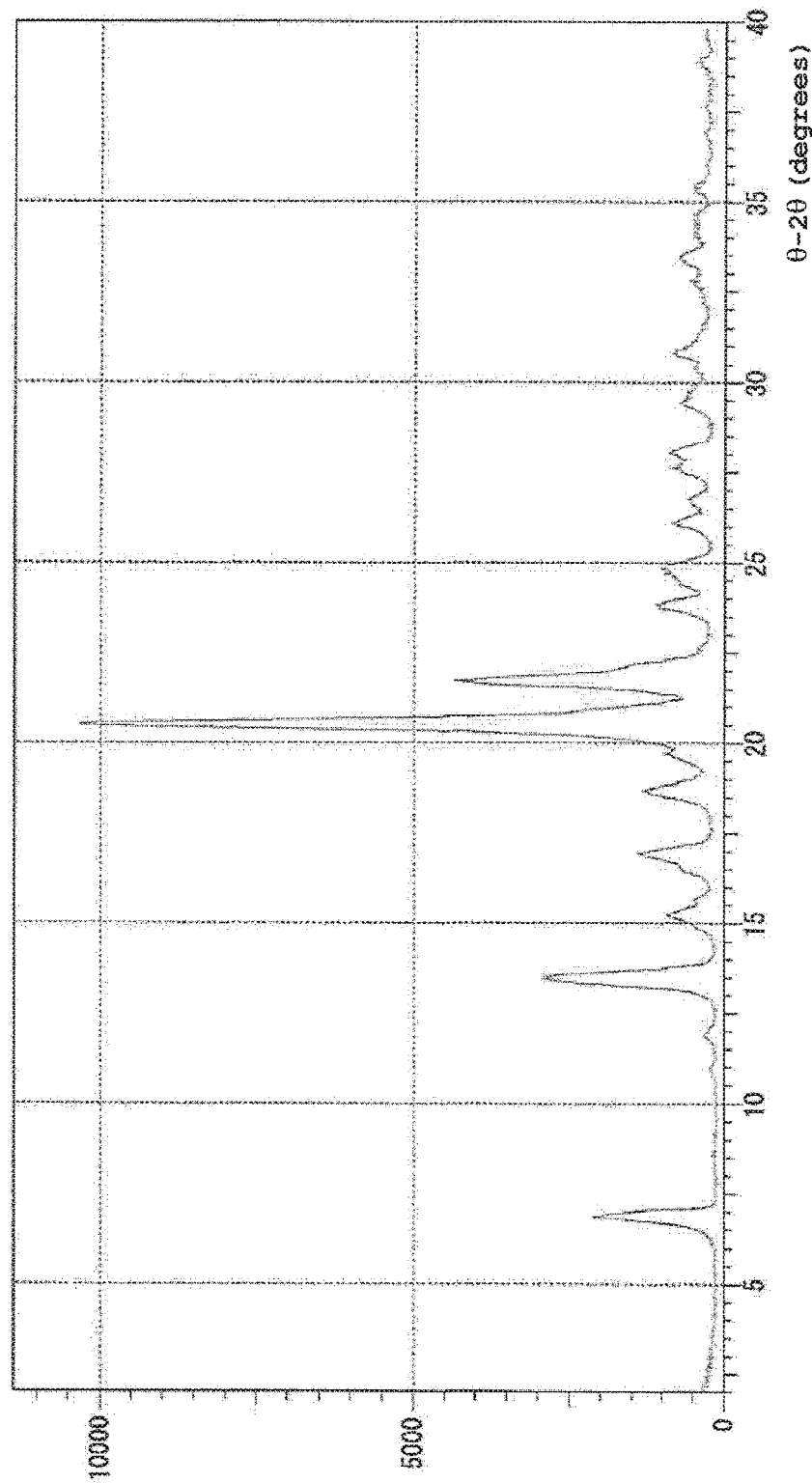

SEQUENCE LISTING

```
<160> NUMBER OF SEQ ID NOS: 10

<210> SEQ ID NO 1
<211> LENGTH: 753
<212> TYPE: DNA
<213> ORGANISM: Ogataea minuta var. nonfermentans
<220> FEATURE:
<221> NAME/KEY: CDS
<222> LOCATION: (1)..(753)

<400> SEQUENCE: 1 atg gct aaa act gtt tac ttc atc gca ggt gct tcc aga ggt atc ggt     48
Met Ala Lys Thr Val Tyr Phe Ile Ala Gly Ala Ser Arg Gly Ile Gly
1               5                   10                  15 ctc gag gtt gct tcc cag ctg agt gca aac cca gac aat tat gtt att     96
Leu Glu Val Ala Ser Gln Leu Ser Ala Asn Pro Asp Asn Tyr Val Ile
            20                  25                  30 gca tcc tat aga tct gaa aag tct gct tca gga ctt ttg gag ctg gca    144
Ala Ser Tyr Arg Ser Glu Lys Ser Ala Ser Gly Leu Leu Glu Leu Ala
        35                  40                  45 aag aag gat aat gtc gac aca att gtg ttg gat att gca agc cag gaa    192
Lys Lys Asp Asn Val Asp Thr Ile Val Leu Asp Ile Ala Ser Gln Glu
    50                  55                  60 tcg att gat gct gtt cca gca cag att tcc aag ctg act gat gga atc    240
Ser Ile Asp Ala Val Pro Ala Gln Ile Ser Lys Leu Thr Asp Gly Ile
65                  70                  75                  80 gat gtt gcc ttg atc aac gct gga att gcc aac gct atg tgt ccg att    288
Asp Val Ala Leu Ile Asn Ala Gly Ile Ala Asn Ala Met Cys Pro Ile
                85                  90                  95 ctc gaa tgt tct aga gag tcc tac act gat cac tgg aca acc aat gcc    336
Leu Glu Cys Ser Arg Glu Ser Tyr Thr Asp His Trp Thr Thr Asn Ala
            100                 105                 110 ttg ggt cca atc atg ctc tac caa gct att cat aag ttc atg ctc cag    384
Leu Gly Pro Ile Met Leu Tyr Gln Ala Ile His Lys Phe Met Leu Gln
        115                 120                 125 aga gag acc aga aaa gtg ttc ttt acc acg agt gct ggt ggt tcc att    432
Arg Glu Thr Arg Lys Val Phe Phe Thr Thr Ser Ala Gly Gly Ser Ile
```

```
cag gct aag ata ccc gtg cct gtg agt ggt tac ggt atg tcc aag gct    480
Gln Ala Lys Ile Pro Val Pro Val Ser Gly Tyr Gly Met Ser Lys Ala
145                 150                 155                 160 gcg ctt aat tat gct gtg aga aaa ctt gct gac gag tgc tac aag gac    528
Ala Leu Asn Tyr Ala Val Arg Lys Leu Ala Asp Glu Cys Tyr Lys Asp
                165                 170                 175 aac ttc act att gtg ttg ctg cat cct ggt ttt gtt aag acg gac atg    576
Asn Phe Thr Ile Val Leu Leu His Pro Gly Phe Val Lys Thr Asp Met
            180                 185                 190 ggt caa agc gcc att cag aag atg tca aat gga aat gct gag ctt ctt    624
Gly Gln Ser Ala Ile Gln Lys Met Ser Asn Gly Asn Ala Glu Leu Leu
        195                 200                 205 gct tac att gac tca atg act att gat gtt cct acc agt gct ggc caa    672
Ala Tyr Ile Asp Ser Met Thr Ile Asp Val Pro Thr Ser Ala Gly Gln
    210                 215                 220 atc gtc ggt gcc att atg acc ttg gac aag cag agc agc ggt aga ttt    720
Ile Val Gly Ala Ile Met Thr Leu Asp Lys Gln Ser Ser Gly Arg Phe
225                 230                 235                 240 atc aac gct gct gac cag ttt gac atg cca ttt                        753
Ile Asn Ala Ala Asp Gln Phe Asp Met Pro Phe
                245                 250

<210> SEQ ID NO 2
<211> LENGTH: 251
<212> TYPE: PRT
<213> ORGANISM: Ogataea minuta var. nonfermentans

<400> SEQUENCE: 2

Met Ala Lys Thr Val Tyr Phe Ile Ala Gly Ala Ser Arg Gly Ile Gly
1               5                   10                  15

Leu Glu Val Ala Ser Gln Leu Ser Ala Asn Pro Asp Asn Tyr Val Ile
            20                  25                  30

Ala Ser Tyr Arg Ser Glu Lys Ser Ala Ser Gly Leu Leu Glu Leu Ala
        35                  40                  45

Lys Lys Asp Asn Val Asp Thr Ile Val Leu Asp Ile Ala Ser Gln Glu
    50                  55                  60

Ser Ile Asp Ala Val Pro Ala Gln Ile Ser Lys Leu Thr Asp Gly Ile
65                  70                  75                  80

Asp Val Ala Leu Ile Asn Ala Gly Ile Ala Asn Ala Met Cys Pro Ile
                85                  90                  95

Leu Glu Cys Ser Arg Glu Ser Tyr Thr Asp His Trp Thr Thr Asn Ala
            100                 105                 110

Leu Gly Pro Ile Met Leu Tyr Gln Ala Ile His Lys Phe Met Leu Gln
        115                 120                 125

Arg Glu Thr Arg Lys Val Phe Phe Thr Thr Ser Ala Gly Gly Ser Ile
    130                 135                 140

Gln Ala Lys Ile Pro Val Pro Val Ser Gly Tyr Gly Met Ser Lys Ala
145                 150                 155                 160

Ala Leu Asn Tyr Ala Val Arg Lys Leu Ala Asp Glu Cys Tyr Lys Asp
                165                 170                 175

Asn Phe Thr Ile Val Leu Leu His Pro Gly Phe Val Lys Thr Asp Met
            180                 185                 190

Gly Gln Ser Ala Ile Gln Lys Met Ser Asn Gly Asn Ala Glu Leu Leu
        195                 200                 205

Ala Tyr Ile Asp Ser Met Thr Ile Asp Val Pro Thr Ser Ala Gly Gln
    210                 215                 220
```

-continued

```
Ile Val Gly Ala Ile Met Thr Leu Asp Lys Gln Ser Ser Gly Arg Phe
225                 230                 235                 240

Ile Asn Ala Ala Asp Gln Phe Asp Met Pro Phe
                245                 250

<210> SEQ ID NO 3
<211> LENGTH: 29
<212> TYPE: DNA
<213> ORGANISM: Artificial Sequence
<220> FEATURE:
<223> OTHER INFORMATION: PCR primer

<400> SEQUENCE: 3
cggaattcat ggctaaaact gtttacttc                                      29

<210> SEQ ID NO 4
<211> LENGTH: 35
<212> TYPE: DNA
<213> ORGANISM: Artificial Sequence
<220> FEATURE:
<223> OTHER INFORMATION: PCR primer

<400> SEQUENCE: 4
gggaagctta ttactaaaat ggcatgtcaa actgg                               35

<210> SEQ ID NO 5
<211> LENGTH: 783
<212> TYPE: DNA
<213> ORGANISM: Bacillus subtilis
<220> FEATURE:
<221> NAME/KEY: CDS
<222> LOCATION: (1)..(783)

<400> SEQUENCE: 5 atg tat ccg gat tta aaa gga aaa gtc gtc gct att aca gga gct gct     48
Met Tyr Pro Asp Leu Lys Gly Lys Val Val Ala Ile Thr Gly Ala Ala
1               5                   10                  15 tca ggg ctc gga aag gcg atg gcc att cgc ttc ggc aag gag cag gca     96
Ser Gly Leu Gly Lys Ala Met Ala Ile Arg Phe Gly Lys Glu Gln Ala
            20                  25                  30 aaa gtg gtt atc aac tat tat agt aat aaa caa gat ccg aac gag gta    144
Lys Val Val Ile Asn Tyr Tyr Ser Asn Lys Gln Asp Pro Asn Glu Val
        35                  40                  45 aaa gaa gag gtc atc aag gcg ggc ggt gaa gct gtt gtc gtc caa gga    192
Lys Glu Glu Val Ile Lys Ala Gly Gly Glu Ala Val Val Val Gln Gly
    50                  55                  60 gat gtc acg aaa gag gaa gat gta aaa aat atc gtg caa acg gca att    240
Asp Val Thr Lys Glu Glu Asp Val Lys Asn Ile Val Gln Thr Ala Ile
65                  70                  75                  80 aag gag ttc ggc aca ctc gat att atg att aat aat gcc ggt ctt gca    288
Lys Glu Phe Gly Thr Leu Asp Ile Met Ile Asn Asn Ala Gly Leu Ala
                85                  90                  95 aat cct gtg cca tct cac gaa atg ccg ctc aag gat tgg gat aaa gtc    336
Asn Pro Val Pro Ser His Glu Met Pro Leu Lys Asp Trp Asp Lys Val
            100                 105                 110 atc ggc acg aac tta acg ggt gcc ttt tta gga agc cgt gaa gcg att    384
Ile Gly Thr Asn Leu Thr Gly Ala Phe Leu Gly Ser Arg Glu Ala Ile
        115                 120                 125 aaa tat ttc gta gaa aac gat atc aag gga aat gtc att aac atg tcc    432
Lys Tyr Phe Val Glu Asn Asp Ile Lys Gly Asn Val Ile Asn Met Ser
    130                 135                 140 agt gtg cac gaa gtg att cct tgg ccg tta ttt gtc cac tat gcg gca    480
Ser Val His Glu Val Ile Pro Trp Pro Leu Phe Val His Tyr Ala Ala
```

```
Ser Val His Glu Val Ile Pro Trp Pro Leu Phe Val His Tyr Ala Ala
145                 150                 155                 160 agt aaa ggc ggg ata aag ctg atg aca gaa aca tta gcg ttg gaa tac        528
Ser Lys Gly Gly Ile Lys Leu Met Thr Glu Thr Leu Ala Leu Glu Tyr
                165                 170                 175 gcg ccg aag ggc att cgc gtc aat aat att ggg cca ggt gcg atc aac        576
Ala Pro Lys Gly Ile Arg Val Asn Asn Ile Gly Pro Gly Ala Ile Asn
            180                 185                 190 acg cca atc aat gct gaa aaa ttc gct gac cct aaa cag aaa gct gat        624
Thr Pro Ile Asn Ala Glu Lys Phe Ala Asp Pro Lys Gln Lys Ala Asp
        195                 200                 205 gta gaa agc atg att cca atg gga tat atc ggc gaa ccg gag gag atc        672
Val Glu Ser Met Ile Pro Met Gly Tyr Ile Gly Glu Pro Glu Glu Ile
    210                 215                 220 gcc gca gta gca gcc tgg ctt gct tcg aag gaa gcc agc tac gtc aca        720
Ala Ala Val Ala Ala Trp Leu Ala Ser Lys Glu Ala Ser Tyr Val Thr
225                 230                 235                 240 ggc atc acg tta ttc gcg gac ggc ggt atg aca caa tat cct tca ttc        768
Gly Ile Thr Leu Phe Ala Asp Gly Gly Met Thr Gln Tyr Pro Ser Phe
                245                 250                 255 cag gca ggc cgc ggt                                                    783
Gln Ala Gly Arg Gly
            260

<210> SEQ ID NO 6
<211> LENGTH: 261
<212> TYPE: PRT
<213> ORGANISM: Bacillus subtilis

<400> SEQUENCE: 6

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Ala
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160
```

```
Ser Lys Gly Gly Ile Lys Leu Met Thr Glu Thr Leu Ala Leu Glu Tyr
            165                 170                 175

Ala Pro Lys Gly Ile Arg Val Asn Asn Ile Gly Pro Gly Ala Ile Asn
        180                 185                 190

Thr Pro Ile Asn Ala Glu Lys Phe Ala Asp Pro Lys Gln Lys Ala Asp
    195                 200                 205

Val Glu Ser Met Ile Pro Met Gly Tyr Ile Gly Glu Pro Glu Glu Ile
210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

<210> SEQ ID NO 7
<211> LENGTH: 37
<212> TYPE: DNA
<213> ORGANISM: Artificial Sequence
<220> FEATURE:
<223> OTHER INFORMATION: PCR primer

<400> SEQUENCE: 7
ggggaattca tgtatccgga tttaaaagga aaagtcg          37

<210> SEQ ID NO 8
<211> LENGTH: 32
<212> TYPE: DNA
<213> ORGANISM: Artificial Sequence
<220> FEATURE:
<223> OTHER INFORMATION: PCR primer

<400> SEQUENCE: 8
gggtctagat taaccgcggc ctgcctggaa tg          32

<210> SEQ ID NO 9
<211> LENGTH: 34
<212> TYPE: DNA
<213> ORGANISM: Artificial Sequence
<220> FEATURE:
<223> OTHER INFORMATION: PCR primer

<400> SEQUENCE: 9
cccaagctta gttaacttta gaaggagaca attc          34

<210> SEQ ID NO 10
<211> LENGTH: 18
<212> TYPE: DNA
<213> ORGANISM: Artificial Sequence
<220> FEATURE:
<223> OTHER INFORMATION: PCR primer

<400> SEQUENCE: 10
ctgccgcccg actatcac          18

METHOD FOR PRODUCING PITAVASTATIN CALCIUM

TECHNICAL FIELD

The present invention relates to an improved production method of pitavastatin calcium.

BACKGROUND ART

Pitavastatin calcium has an activity to specifically and antagonistically inhibit HMG-CoA reductase which is a rate determining enzyme of cholesterol synthesis, and is used for the treatment of hypercholesterolemia, familial hypercholesterolemia and the like.

Pitavastatin calcium has a chemical name: bis[(3R,5S,6E)-7-[2-cyclopropyl-4-(4-fluorophenyl)-3-quinolyl]-3,5-dihydroxy-6-heptenoate]-calcium represented by the following formula:

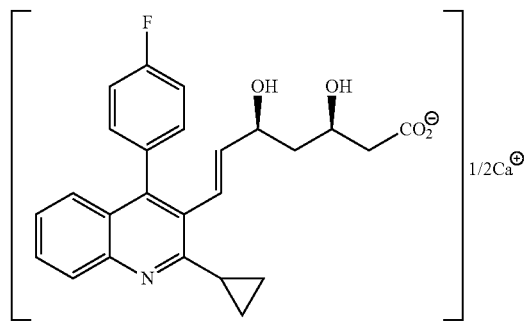

It is known that pitavastatin calcium can be produced by hydrolyzing a precursor compound thereof, 2-[(4R,6S)-6-[(E)-[2-cyclopropyl-4-(4-fluorophenyl)-3-quinolyl]vinyl]-2,2-dimethyl-1,3-dioxan-4-yl]acetate ester represented by the following formula (16):

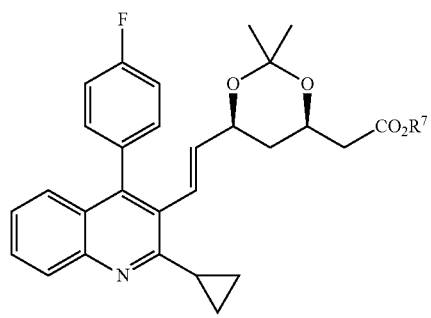

wherein $R^7$ is an alkyl group having a carbon number of 1-4.

A compound represented by the formula (16) can be obtained by a Wittig reaction.

Patent document 1 describes that the above-mentioned compound represented by the formula (16) can be obtained by reacting a condensed pyridine derivative and an aldehyde compound in the presence of n-butyllithium at −78° C.

The method described in patent document 1 requires a special facility for industrial production since the reaction is performed at an extremely low temperature of −78° C., and the yield thereof is low. In addition, since n-butyllithium, which is liable to ignite easily, is used as a base, there is concern about safety in industrial-scale production. Furthermore, since n-butyllithium and phosphorus tribromide used for the reaction are expensive, the cost becomes high.

Patent document 2 describes that the above-mentioned compound represented by the formula (16) is obtained by reacting a compound represented by the following formula (17):

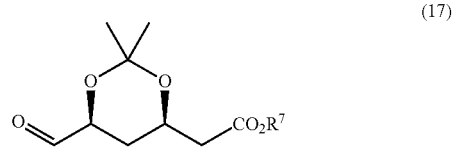

wherein $R^7$ is as defined above and a compound represented by the following formula (18):

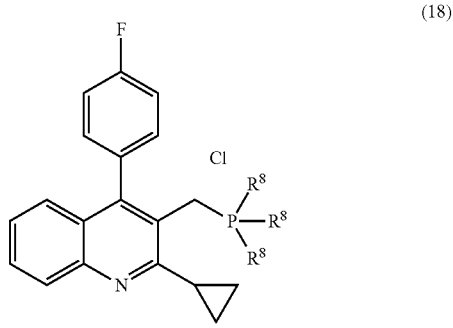

wherein $R^8$ is an aryl group, aralkyl group or alkyl group, in the presence of an alkali metal salt.

The method described in patent document 2 has an insufficient yield for industrial production. In addition, the compound represented by the formula (17) and the compound represented by the formula (18) require multistep process for synthesis, which produces concern about the costs.

DOCUMENT LIST

Patent Documents patent document 1: JP-A-5-310700
patent document 2: JP-A-2014-1176

SUMMARY OF THE INVENTION

Problems to be Solved by the Invention

The development of a method for producing pitavastatin calcium safely on an industrial scale with a high yield and high selectivity at low cost has been desired.

The problem to be solved by the present invention is to provide a method for producing highly pure pitavastatin calcium on an industrial scale, whose method is superior in safety and cost and affords a high yield and high selectivity.

Means of Solving the Problems

The present inventors have conducted intensive studies and found that the above-mentioned problem can be solved by using a particular intermediate compound, which resulted in the completion of the present invention. That is, the gist of the present invention is as follows.

[1] A method for producing pitavastatin calcium comprising
(i) a step of acetalizing a compound represented by the following formula (1):

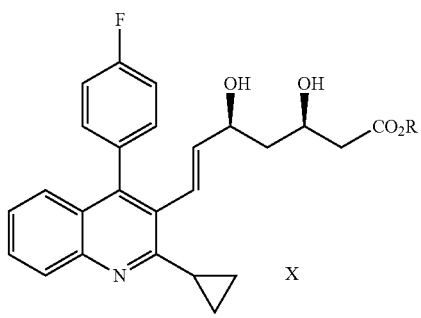

wherein R is a straight chain alkyl group having a carbon number of 1-8 or a branched alkyl group having a carbon number of 3-8 and X is an acid, to give a compound represented by the following formula (3):

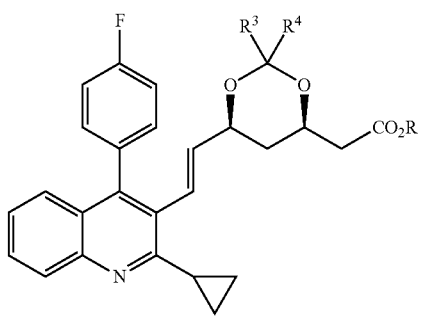

wherein $R^3$ and $R^4$ are each independently an alkyl group having a carbon number of 1-4 and R is as defined above;
(ii) a step of reacting the above-mentioned compound represented by the formula (3) with an acid to give a compound represented by the following formula (4)

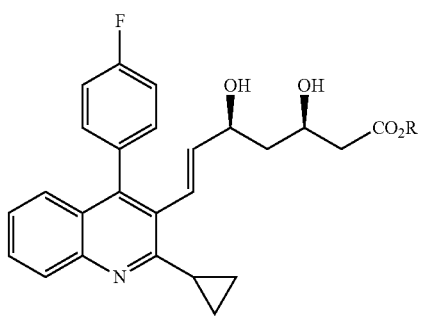

wherein R is as defined above; and
(iii) a step of hydrolyzing the above-mentioned compound represented by the formula (4) and reacting the compound with a calcium compound to give pitavastatin calcium.

[2] The production method of [1] further comprising
(iv) a step of reacting a compound represented by the following formula (6):

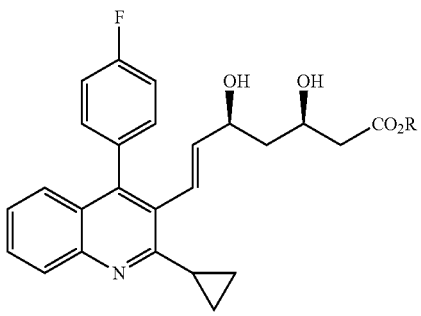

wherein R is a straight chain alkyl group having a carbon number of 1-8 or a branched alkyl group having a carbon number of 3-8, with an acid to give a compound represented by the following formula (1):

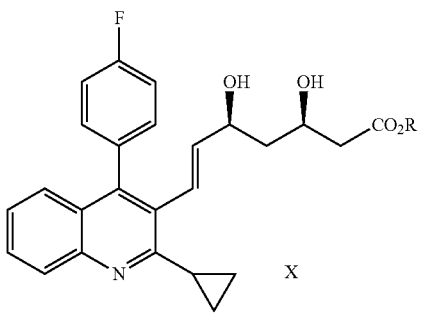

wherein X is an acid and R is as defined above.

[3] The production method of [2], comprising
(v) a step of condensing a compound represented by the following formula (7)

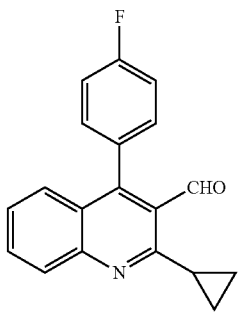

and a compound represented by the following formula (8):

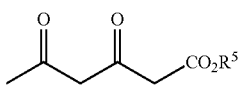

wherein $R^5$ is a straight chain alkyl group having a carbon number of 1-8 or a branched alkyl group having a carbon number of 3-8 provided $R^5$ is different from R in the above-mentioned formula (1), in the presence of a base to give a compound represented by the following formula (9):

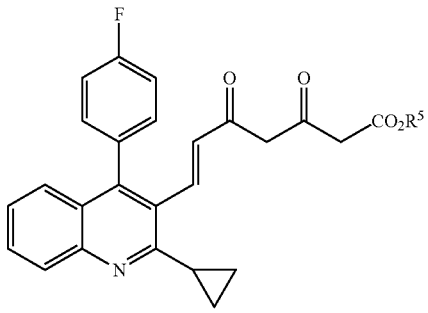

(9)

wherein $R^5$ is as defined above;

(vi) a step of reacting the above-mentioned compound represented by the formula (9) obtained in step (v) with alcohol represented by R—OH wherein R is a straight chain alkyl group having a carbon number of 1-8 or a branched alkyl group having a carbon number of 3-8 to give a compound represented by the following formula (10):

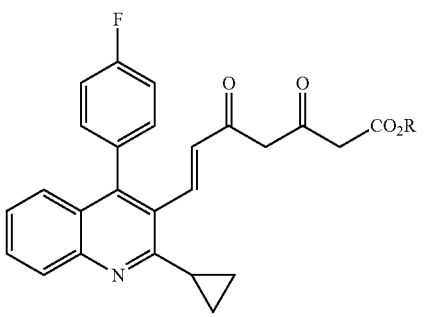

(10)

wherein R is as defined above; and (vii) a step of reacting the above-mentioned compound represented by the formula (10) obtained in step (vi) with an enzyme having an activity capable of stereoselectively reducing a carbonyl group, a microorganism or cell having an ability to produce the enzyme, a treated product of the microorganism or cell, and/or a culture solution containing the enzyme obtained by culturing the microorganism or cell to give a compound represented by the following formula (6)

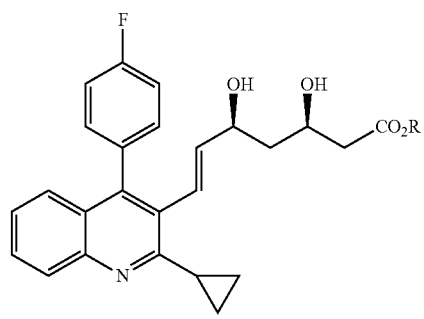

(6)

wherein R is as defined above.

[4] The production method of [2], comprising (viii) a step of reacting a compound represented by the following formula (12):

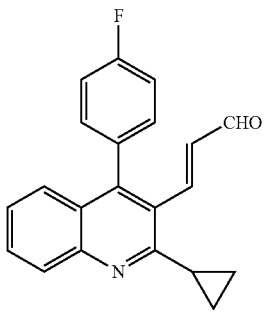

(12)

in the presence of a titanium catalyst with a compound represented by the following formula (13):

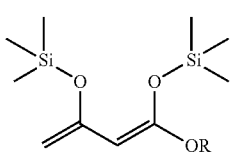

(13)

wherein R is a straight chain alkyl group having a carbon number of 1-8 or a branched alkyl group having a carbon number of 3-8, to give a compound represented by the following formula (14):

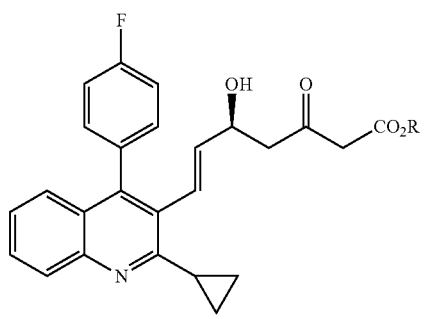

(14)

wherein R is as defined above; and (ix) a step of reacting the above-mentioned compound a represented by the formula (14) obtained in step (viii) with an enzyme having an activity capable of stereoselectively reducing a carbonyl group, a microorganism or cell having an ability to produce the enzyme, a treated product of the microorganism or cell, and/or a culture solution containing the enzyme obtained by culturing the microorganism or cell to give a compound represented by the following formula (6):

(6)

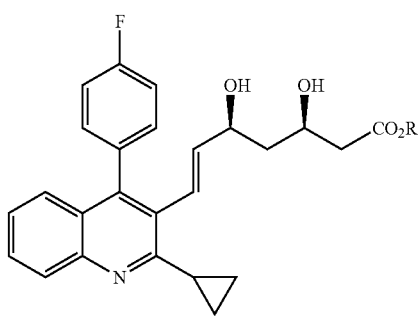

wherein R is as defined above.

[5] A compound represented by the following formula (1'):

(1')

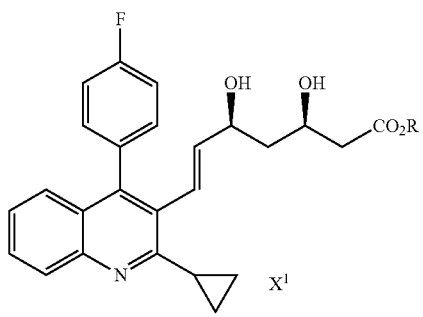

wherein R is a straight chain alkyl group having a carbon number of 1-8 or a branched alkyl group having a carbon number of 3-8 and $X^1$ is methanesulfonic acid.

[6] A method for producing a compound represented by the following formula (1):

(1)

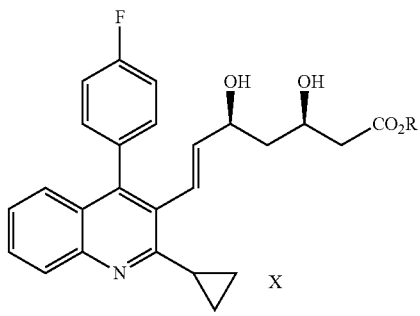

wherein X is an acid and R is a straight chain alkyl group having a carbon number of 1-8 or a branched alkyl group having a carbon number of 3-8, comprising (iv) reacting a compound represented by the following formula (6):

(6)

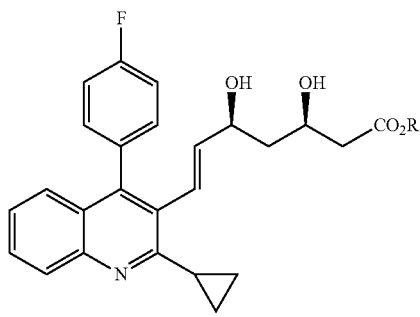

wherein R is as defined above, with an acid.

Also, the gist of the present invention is as follows.

[1A] A method for producing pitavastatin calcium represented by the following formula (5):

(5)

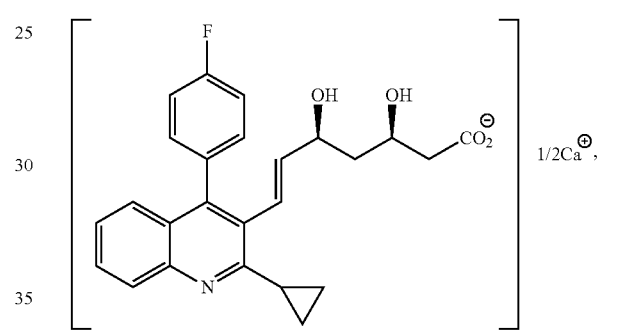

comprising (i) a step of acetalizing a compound represented by the following formula (i):

(1)

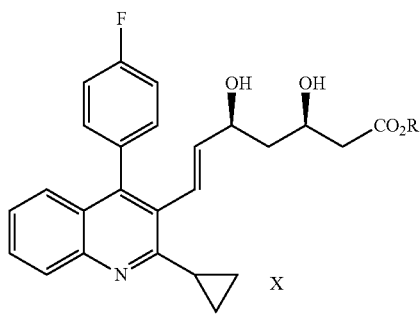

wherein R is a straight chain alkyl group having a carbon number of 1-8 or a branched alkyl group having a carbon number of 3-8 and X is an acid, to give a compound represented by the following formula (3):

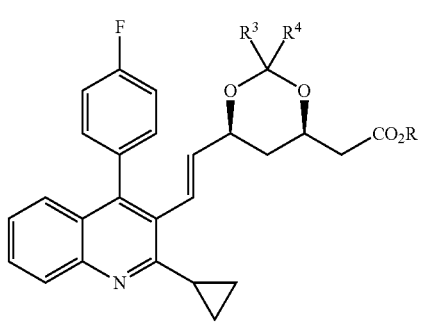

(3)

wherein $R^3$ and $R^4$ are each independently an alkyl group having a carbon number of 1-4 and R is as defined above;

(ii) a step of reacting a compound represented by the following formula (3):

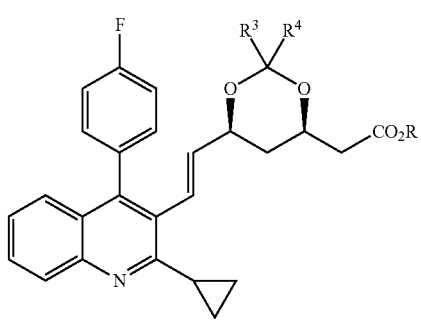

(3)

wherein R, $R^3$ and $R^4$ are as defined above, with an acid catalyst to give a compound represented by the following formula (4):

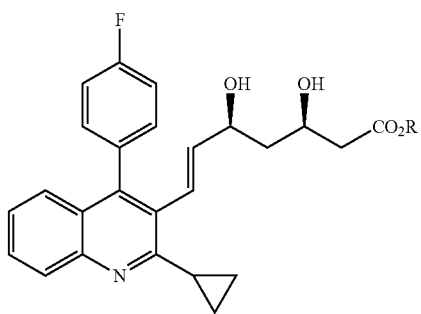

(4)

wherein R is as defined above; and (iii) a step of hydrolyzing a compound represented by the following formula (4):

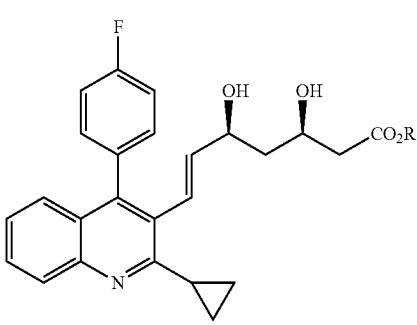

(4)

wherein R is as defined above, and reacting the compound with a calcium compound.

[2A] The production method of [1A] comprising (iv) a step of reacting a compound represented by the following formula (6):

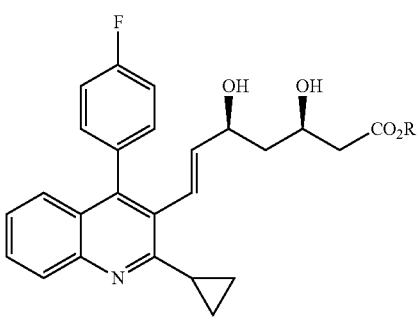

(6)

wherein R is as defined above, with an acid.

[3] The production method of [2A], comprising (v) a step of condensing a compound represented by the following formula (7):

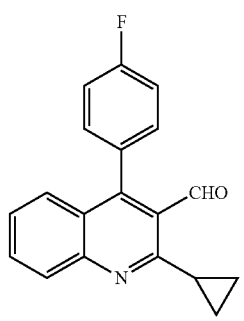

(7)

and a compound represented by the following formula (8):

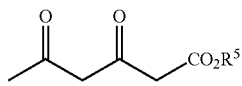

(8)

wherein $R^5$ is a straight chain alkyl group having a carbon number of 1-8 or a branched alkyl group having a carbon number of 3-8, provided $R^5$ is different from R, in the presence of a base to give a compound represented by the following formula (9):

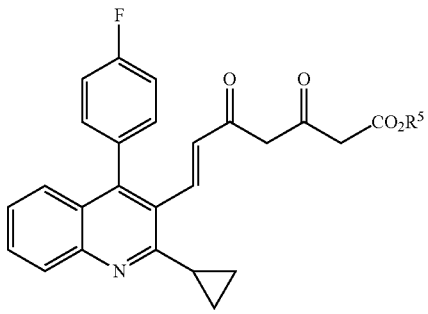

(9)

wherein $R^5$ is as defined above;
(vi) a step of reacting the above-mentioned compound represented by the formula (9) obtained in step (v) with alcohol represented by R—OH wherein R is as defined above to give a compound represented by the following formula (10):

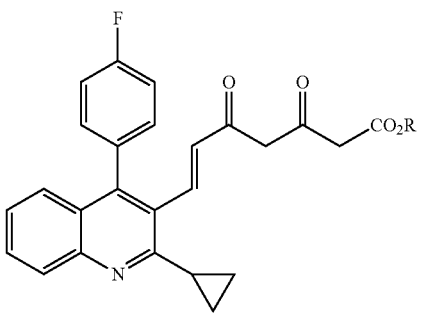

(10)

wherein R is as defined above; and
(vii) a step of reacting the above-mentioned compound represented by the formula (10) obtained in step (vi) with an enzyme having an activity capable of stereoselectively reducing a carbonyl group, a microorganism or cell having an ability to produce the enzyme, a treated product of the microorganism or cell, and/or a culture solution containing the enzyme obtained by culturing the microorganism or cell to give a compound represented by the following formula (6):

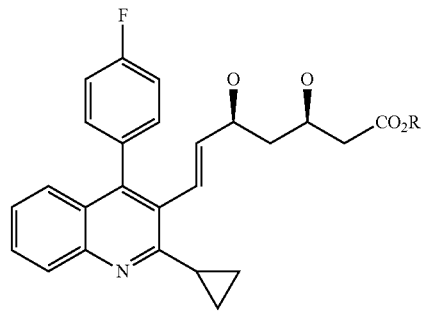

(6)

wherein R is as defined above.

[4A] The production method of [2A], comprising
(viii) a step of reacting a compound represented by the following formula (12)

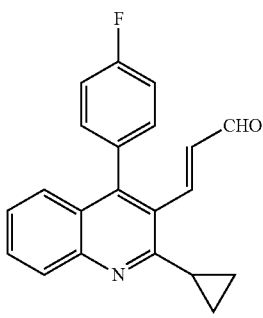

(12)

in the presence of a Ti catalyst with a compound represented by the following formula (13):

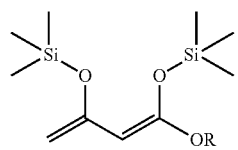

(13)

to give a compound represented by the following formula (14):

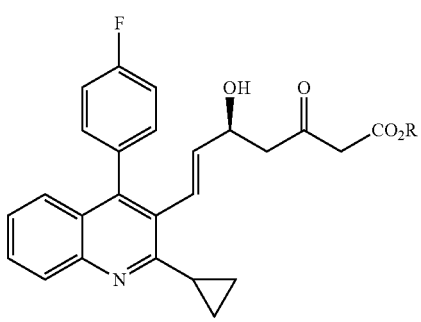

(14)

wherein R is as defined above; and
(ix) a step of reacting the above-mentioned compound represented by the formula (14) obtained in step (viii) with an enzyme having an activity capable of stereoselectively reducing a carbonyl group, a microorganism or cell having an ability to produce the enzyme, a treated product of the microorganism or cell, and/or a culture solution containing the enzyme obtained by culturing the microorganism or cell to give a compound represented by the following formula (6):

(6)

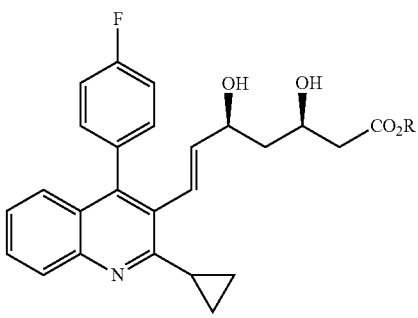

wherein R is as defined above.

[5A] A compound represented by the following formula (1):

(1)

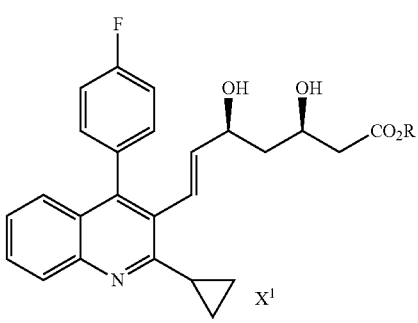

wherein R is a straight chain alkyl group having a carbon number of 1-8 or a branched alkyl group having a carbon number of 3-8 and $X^1$ is methanesulfonic acid.

[6A] A method for producing a compound represented by the following formula (1)

(1)

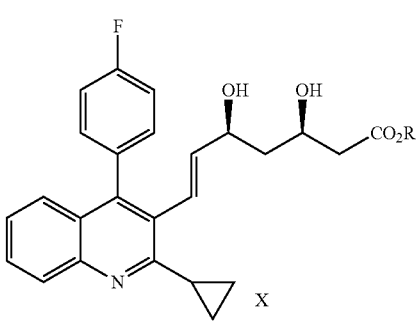

wherein X is an acid and R is a straight chain alkyl group having a carbon number of 1-8 or a branched alkyl group having a carbon number of 3-8, comprising (iv) reacting a compound represented by the following formula (6):

(6)

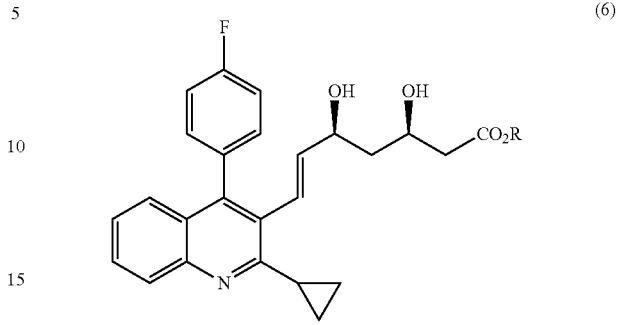

wherein R is as defined above, with an acid.

Effect of the Invention

The production method of the present invention enables safe production of pitavastatin calcium on an industrial scale in a high yield with high selectivity at a low cost.

BRIEF DESCRIPTION OF THE DRAWINGS

FIG. 1 is an X ray diffraction chart of DOLE MsOH obtained in Example 5.

DESCRIPTION OF EMBODIMENTS

The terms used in the present specification are explained in detail in the following.

R is a straight chain alkyl group having a carbon number of 1-8 or a branched alkyl group having a carbon number of 3-8, preferably a straight chain alkyl group having a carbon number of 1-8, more preferably a straight chain alkyl group having a carbon number of 1-4, particularly preferably a methyl group, an ethyl group or an n-propyl group.

$R^1$, $R^2$, $R^3$ and $R^4$ are each independently an alkyl group having a carbon number of 1-4, preferably a straight chain alkyl group having a carbon number of 1-4, particularly preferably a methyl group, an ethyl group or an n-propyl group. In addition, $R^1$ and $R^2$ may be linked to form a ring.

$R^5$ is a straight chain alkyl group having a carbon number of 1-8 or a branched alkyl group having a carbon number of 3-8, provided R is different from R. $R^5$ is preferably a branched alkyl group having a carbon number of 3-8, more preferably an isopropyl group, an s-butyl group, a tert-butyl group, a tert-amyl group, particularly preferably a tert-butyl group.

Ra is an alkyl group having a carbon number of 1-10. Ra is preferably a lower alkyl group having a carbon number of 1-4 such as methyl group, ethyl group, propyl group, isopropyl group, butyl group, t-butyl group and the like, and industrially, an isopropyl group is particularly preferably.

X is an acid, preferably a mineral acid such as sulfuric acid, hydrochloric acid and the like; an organic acid such as formic acid, acetic acid, methanesulfonic acid, p-toluenesulfonic acid or the like, more preferably, sulfuric acid, hydrochloric acid, methanesulfonic acid or p-toluenesulfonic acid, particularly preferably methanesulfonic acid.

$X^1$ is methanesulfonic acid.

In the present specification, the "enzyme having an activity capable of stereoselectively reducing a carbonyl group" means an enzyme having an activity to convert a carbonyl group in a carbonyl group-containing compound to optically active alcohol by asymmetric reduction.

Whether the "activity capable of reducing a carbonyl group stereoselectively" is present can be determined by measuring an activity to convert a carbonyl group in a carbonyl group-containing compound to an optically active alcohol by asymmetric reduction by a general assay method. For example, a measurement target enzyme is reacted with a compound represented by the following formula (19):

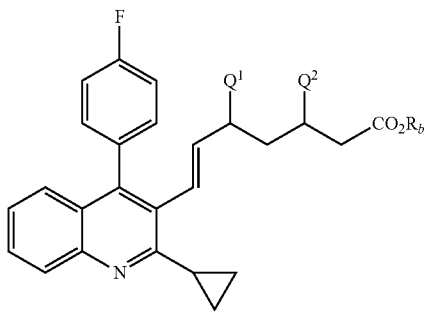

(19)

wherein $R_b$ is a straight chain alkyl group having a carbon number of 1-8 or a branched alkyl group having a carbon number of 3-6, $-Q^1$ and $-Q^2$ are each independently —OH or =O, and at least one of $-Q^1$ and $-Q^2$ is =O, and the amount of a compound represented by the formula (6) converted from the compound represented by the formula (19) is directly measured, whereby the enzyme activity can be confirmed.

The "enzyme" in the present specification includes purified enzyme (including partially purified enzyme), an enzyme immobilized on a carrier and the like by a conventional immobilization technique, for example, one immobilized on a carrier such as polyacrylamide, carageenan gel and the like.

In the present specification, the "microorganism or cell capable of producing an enzyme having an activity capable of reducing a carbonyl group stereoselectively" (hereinafter sometimes referred to as "the microorganism or cell of the present invention") is not particularly limited as long as it has an "activity capable of reducing a carbonyl group stereoselectively", and it may be a microorganism or cell inherently having the aforementioned activity, or a microorganism or cell imparted with the aforementioned activity by bleeding. As a means for imparting the aforementioned activity by bleeding, known methods such as a gene recombinant treatment (transformation), a mutation treatment and the like can be adopted. As a method of transformation, methods such as introduction of the object gene, enhanced expression of an enzyme gene in the biosynthetic pathway of organic compounds, reduction of expression of an enzyme gene in the by-product biosynthetic pathway and the like can be used.

As the kind of the "microorganism or cell of the present invention", those described in the below-mentioned host organism or host cell can be mentioned. A "microorganism or cell of the present invention" in a state of being frozen can also be used. In the present specification, the "microorganism or cell capable of producing an enzyme having the activity" is not limited to a living microorganism or cell, but also includes one which is biologically dead but has an enzymatic activity.

The microorganism or cell in the present invention can be produced, for example, by the method described in WO 2003/078634.

In the present specification, the kind of the organism to be a "host organism" is not particularly limited, and prokaryotes such as Escherichia coli, Bacillus subtilis, corynebacterium, Pseudomonas bacterium, Bacillus bacterium, Rhizobium bacterium, Lactobacillus bacterium, Succinobacillus bacterium, Anaerobiospirillum bacterium, Actinobacillus bacterium and the like, fungi such as yeast, filamentous fungi and the like, eucaryotes such as plant, animal and the like can be mentioned. Of these, preferred are Escherichia coli, yeast and corynebacterium, and particularly preferred is Escherichia coli.

In the present specification, the kind of the cell to be a "host cell" is not particularly limited, and animal cell, plant cell, insect cell and the like can be used.

In the present specification, an "expression vector" is a genetic factor used for replicating and expressing a protein having a desired function in the aforementioned host organism, by introducing a polynucleotide encoding a protein having a desired function into a host organism. Examples thereof include, but are not limited to, plasmid, virus, phage, cosmid and the like. Preferable expression vector is a plasmid.

In the present specification, a "transformant" means a microorganism or cell into which the aforementioned expression vector has been introduced, and which has acquired an ability to show a desired trait associated with a protein having a desired function.

In the present specification, a "treated product of microorganism or cell" means a product obtained by culturing a microorganism or cell, and 1) treating the microorganism or cell with an organic solvent and the like, 2) freeze-drying same, 3) immobilizing same on a carrier and the like, 4) physical or enzymatical destruction and containing a protein having a desired function and the like.

In the present specification, a "culture medium containing enzyme obtained by culturing microorganism or cell" means 1) a culture medium of microorganism or cell, 2) a culture medium obtained by treating a culture medium of microorganism or cell with an organic solvent and the like, or 3) a culture medium wherein cellular membrane of microorganism or cell is physically or enzymatically destroyed.

The production method of pitavastatin calcium of the present invention is explained in detail below. In the following, w/v means weight/volume.

The production method of pitavastatin calcium of the present invention includes, as shown below, step (i) for acetalizing a compound represented by the formula (1) to give a compound represented by the formula (3), step (ii) for reacting a compound represented by the formula (3) with an acid to give a compound represented by the formula (4), and step (iii) for hydrolyzing a compound represented by the formula (4) and reacting same with a calcium compound to give pitavastatin calcium represented by the formula (5).

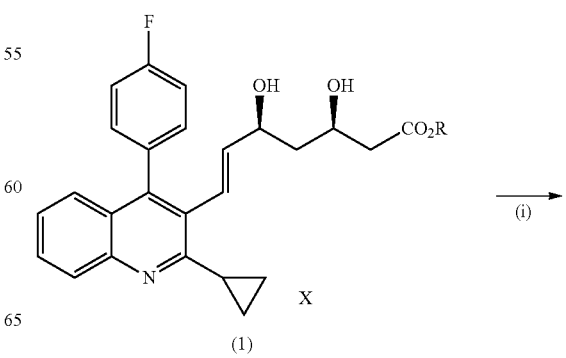

(1)

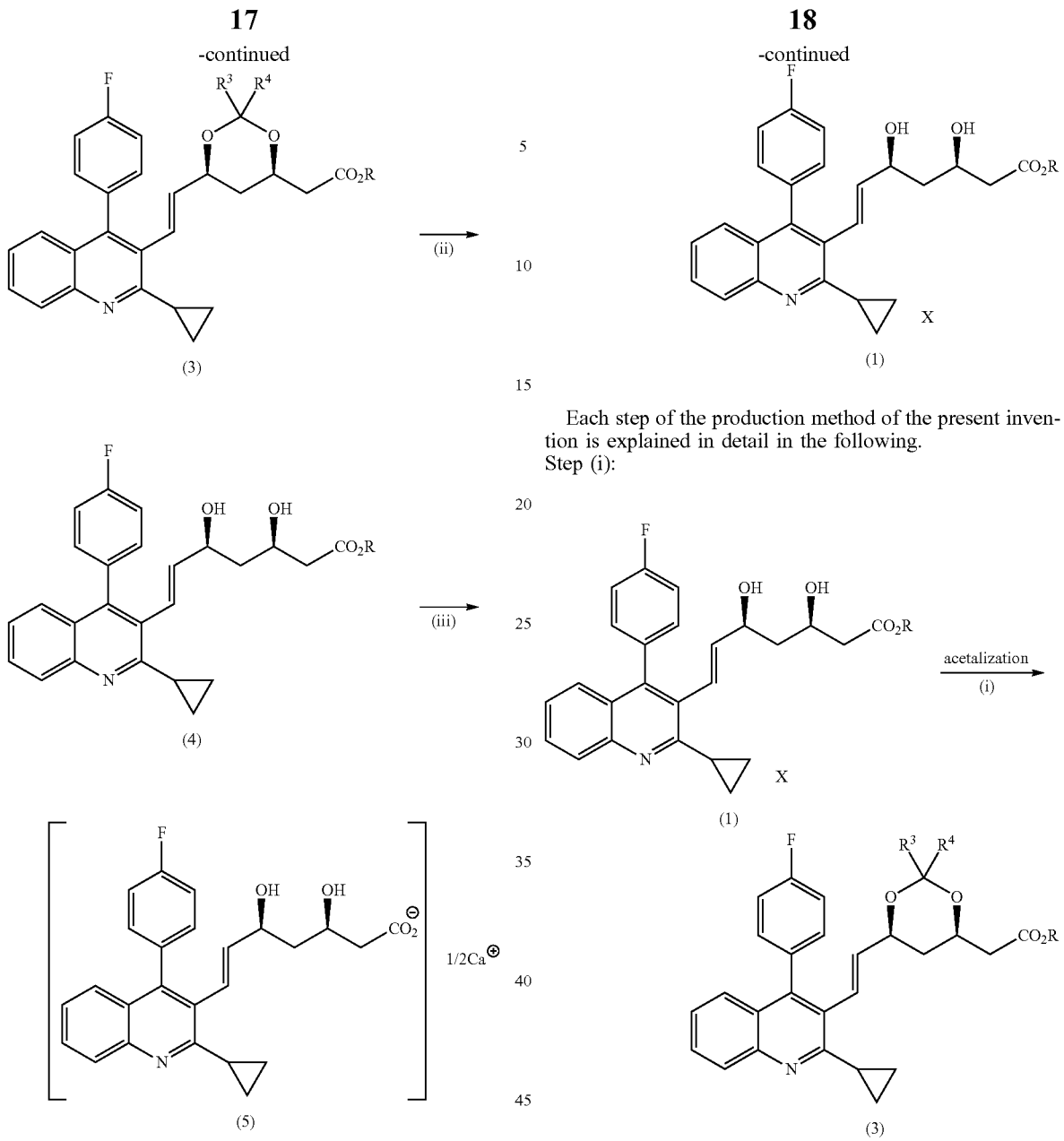

in addition, a compound represented by the formula (1) can also be obtained by reacting a compound represented by the formula (6) with an acid.

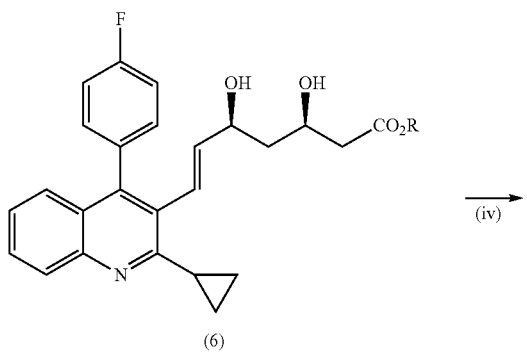

Each step of the production method of the present invention is explained in detail in the following.

Step (i):

In step (i), a compound represented by the formula (1) is acetalized to give a compound represented by the formula (3).

Specifically, a compound represented by the formula (1) is reacted with an acetalizing agent represented by the following formula (2-1) or (2-2).

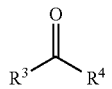

The amount of the acetalizing agent to be used is not particularly limited, and it is generally 1 mol-10 mol, 0.0 preferably 1 mol-6 mol, relative to 1 mol of a compound represented by the formula (1).

The reaction may be performed in the presence of an acid catalyst.

As the acid catalyst, mineral acids such as sulfuric acid, hydrochloric acid and the like; organic acids such as formic acid, acetic acid, p-toluenesuifonic acid, pyridinium p-toluenesulfonate and the like; solid acids such as zeolite and the like, and the like can be used. One kind of these may be used or a mixture of two or more kinds thereof may also be used. Of these, p-toluenesulfonic acid, methanesulfonic acid or pyridinium p-toluenesulfonate is industrially preferable.

When an acid catalyst is used, it may be dissolved in the below-mentioned solvent and used.

While the amount of the acid catalyst to be used is not particularly limited, and it is generally 0.001 mol-2 mol, preferably 0.01 mol-1.5 mol, relative to 1 mol of a compound represented by the formula (1).

The reaction with an acetalizing agent is preferably performed using a solvent. While the solvent is not particularly limited as long as the reaction proceeds, hydrocarbon solvents such as cyclohexane, n-hexane, n-heptane, toluene and the like; ether solvents such as tert-butyl methyl ether, tetrahydrofuran (THF), cyclopentyl methyl ether (CPME) and the like; ester solvents such as ethyl acetate, propyl acetate, butyl acetate and the like; alcohol solvents such as methanol, ethanol, n-propanol and the like; ketone solvents such as acetone, methylethyl ketone and the like; acetonitrile and the like are preferably used. One kind of these solvents may be used or a mixture of two or more kinds thereof may also be used.

The amount of the solvent to be used is not particularly limited, and it is generally 1 mL-100 mL, preferably 1 mL-20 mL, relative to 1 g of a compound represented by the formula (1).

A reaction temperature lower than the boiling point of the solvent to be used and higher than the melting point of the solvent to be used hardly influences the reaction or the yield of the object product. Thus, the reaction temperature can be appropriately selected from this temperature range. Industrially, it is preferably 0° C.-80° C., more preferably 10° C.-70° C.

The reaction time is generally 0.5 hr-24 hr, preferably 1 hr-12 hr.

In addition, it is also possible to produce a compound represented by the formula (3) having a low epimer content percentage by further reacting the resultant reaction product containing a compound represented by the formula (3) obtained in step (i) with an acid to partially decompose the acetal moiety of the compound represented by the formula (3).

As the acid, mineral acids such as sulfuric acid, hydrochloric acid and the like; organic acids such as formic acid, acetic acid, p-toluenesulfonic acid, methanesulfonic acid, pyridinium p-toluenesulfonate and the like can be used. One kind of these may be used or a mixture of two or more kinds thereof may also be used. Of these, sulfuric acid, hydrochloric acid or methansulfonic acid is industrially preferable. The acid may be used as an aqueous solution, or may be dissolved in the below-mentioned solvent and used.

The amount of the acid to be used is not particularly limited, and it is generally 0.01 mol-1 mol, preferably 0.05 mol-0.5 mol, relative to 1 mol of a compound represented by the formula (3).

The reaction with acid is preferably performed using a solvent. While the solvent is not particularly limited as long as the reaction proceeds, hydrocarbon solvents such as cyclohexane, n-hexane, n-heptane, toluene and the like; ether solvents such as tert-butyl methyl ether, tetrahydrofuran (THF), cyclopentyl methyl ether (CPME) and the like; ester solvents such as ethyl acetate, propyl acetate, butyl acetate and the like; alcohol solvents such as methanol, ethanol, n-propanol and the like; ketone solvents such as acetone, methylethyl ketone and the like; acetonitrile and the like are preferably as used. One kind of these solvents may be used or a mixture of two or more kinds thereof may also be used.

The amount of the solvent to be used is not particularly limited, and it is generally 1 mL-100 mL, preferably 1 mL-20 mL, relative to 1 g of a compound represented by the formula (1).

A reaction temperature lower than the boiling point of the solvent to be used and higher than the melting point of the solvent to be used hardly influences the reaction or the yield of the object product. Thus, the reaction temperature can be appropriately selected from this temperature range. Industrially, it is preferably 0° C.-60° C., more preferably 10° C.-50° C.

The epimer content percentage can be controlled by the degree of progress of the reaction and, for example, the epimer so content percentage can be set to 0.3% or below by performing the reaction such that the conversion ratio would be 5%-30%.

A compound represented by the formula (3) obtained in step (i) may be directly used in step (ii), or may be used in step (ii) after decreasing the epimer content percentage as mentioned above, or may be used in step (ii) after purification.

As the purification method, purification by column chromatography, crystallization and the like can be combined appropriately. In the case of column chromatography, for example, non-polar solvents such as n-heptane, n-hexane, toluene and the like and polar solvents such as ethyl acetate, methylethyl ketone, THF, ethanol and the like are combined to perform purification. In the case of crystallization, for example, a non-polar solvent such as n-heptane, n-hexane, toluene and the like or water and a polar solvent such as ethyl acetate, methylethyl ketone, THF, methanol, ethanol, n-propanol and the like are combined to perform purification.

In addition, a compound of the formula (1) wherein X is methanesulfonic acid (methanesulfonate) is preferable since a compound represented by the formula (3) is crystallized by merely adding water to the reaction system after the completion of step (i) or after decreasing the epimer content percentage and a compound represented by the formula (3) can be obtained easily. When water is added, a compound represented by the formula (3) obtained separately may be used as a seed crystal to facilitate crystallization. During crystallization, a base may be added to neutralize the system. As the base, inorganic salts such as sodium hydrogen carbonate, potassium hydrogen carbonate and the like, organic bases such as triethylamine and the like can be mentioned, and preferred are sodium hydrogen carbonate and potassium hydrogen carbonate.

Step (ii):

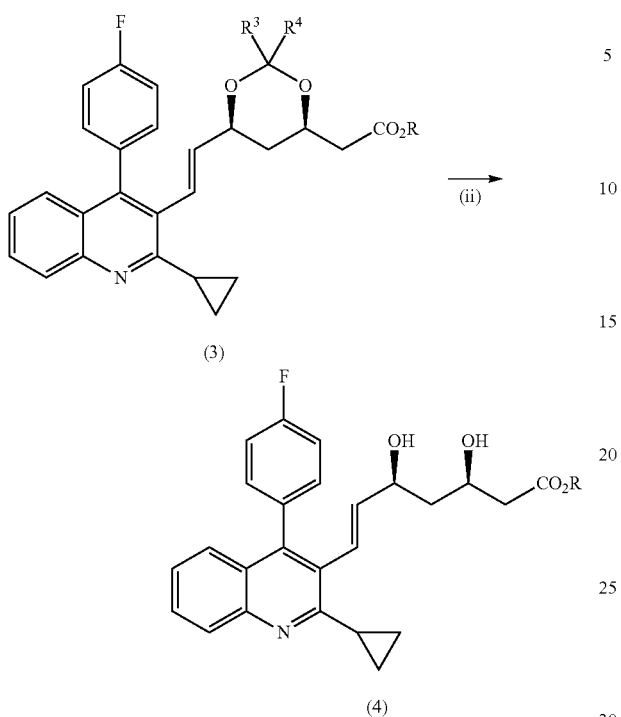

In step (ii), a compound represented by the formula (3) is reacted with an acid for deacetalization to give a compound represented by the formula (4).

As the acid, mineral acids such as sulfuric acid, hydrochloric acid and the like; and organic acids such as formic acid, acetic acid, p-toluenesulfonic acid, pyridinium p-toluenesulfonate and the like can be used. One kind of these may be used or a mixture of two or more kinds thereof may also be used. Of these, sulfuric acid or hydrochloric acid is industrially preferable.

The acid may be used as an aqueous solution, or may be dissolved in the below-mentioned solvent and used.

The amount of the acid to be used is not particularly limited, and it is generally 1 mol-5 mol, preferably 1 mol-2 mol, relative to 1 mol of a compound represented by the formula (3).

The reaction with acid is preferably performed using a solvent. While the solvent is not particularly limited as long as the reaction proceeds, hydrocarbon solvents such as cyclohexane, n-hexane, n-heptane, toluene and the like; ether solvents such as tert-butyl methyl ether, tetrahydrofuran (THF), cyclopentyl methyl ether (CPME) and the like; ester solvents such as ethyl acetate, propyl acetate, butyl acetate and the like; alcohol solvents such as methanol, ethanol and the like; ketone solvents such as acetone, methylethyl ketone and the like; and the like are preferably used. One kind of these solvents may be used or a mixture of two or more kinds thereof may also be used.

The amount of the solvent to be used is not particularly so limited, and it is generally 1 mL-100 mL, preferably 1 mL-20 mL, relative to 1 g of a compound represented by the formula (3).

A reaction temperature lower than the boiling point of the solvent to be used and higher than the melting point of the solvent to be used hardly influences the reaction or the yield of the object product. Thus, the reaction temperature can be appropriately selected from this temperature range. Industrially, it is preferably 0° C.-70° C., more preferably 10° C.-50° C.

The reaction time is generally 1 hr-10 hr, preferably 1 hr-5 hr.

Step (iii):

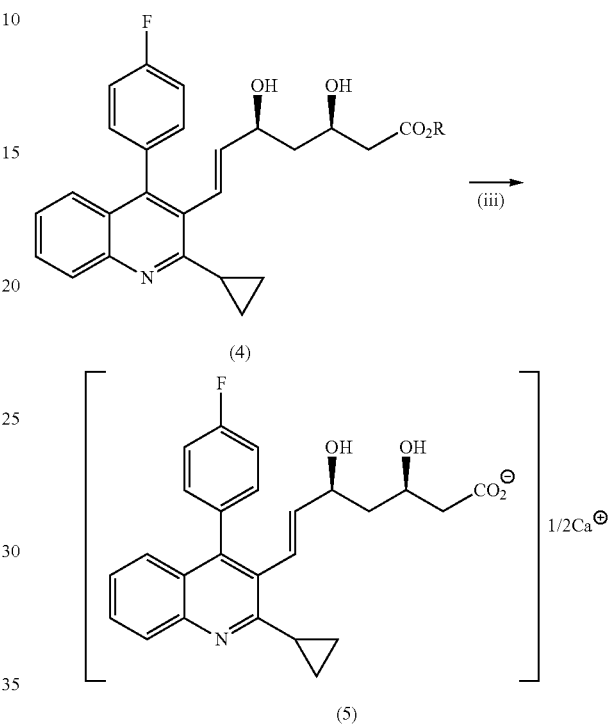

In step (iii), a compound represented by the formula (4) is hydrolyzed and reacted with a calcium compound to give pitavastatin calcium represented by the formula (5). Preferably, a compound represented by the formula (4) is hydrolyzed by reacting with an alkali catalyst and the obtained compound is reacted with a calcium compound to give pitavastatin calcium. Generally, pitavastatin calcium is precipitated as crystals, and therefore, the precipitated pitavastatin calcium is filtered and dried. As the alkali catalyst, an inorganic base can be used and preferably, alkali metal hydroxides such as lithium hydroxide, sodium hydroxide, potassium hydroxide and the like can be used. Industrially, sodium hydroxide is particularly preferable.

The amount of the alkali catalyst to be used is not particularly limited and it is generally 1 mol-2 mol, preferably 1 mol-1.5 mol, relative to 1 mol of a compound represented by the formula (4).

Hydrolysis is preferably performed using a solvent. As the solvent, water is preferable. Where necessary, ether solvents such as THF, 1,4-dioxane and the like; alcohol solvents such as methanol, ethanol and the like; ketone solvents such as acetone and the like may be further added. One kind of these solvents may be used or a mixture of two or more kinds thereof may also be used.

The amount of the solvent to be used is not particularly limited, and it is generally 1 mL-100 mL, preferably 1 mL-50 mL, relative to 1 g of a compound represented by the formula (4).

A hydrolysis temperature lower than the boiling point of the solvent to be used and higher than the melting point of the solvent to be used hardly influences the hydrolysis or the yield of the object product. Thus, the hydrolysis temperature can be appropriately selected from this temperature range. Industrially, it is preferably 0° C.-70° C., more preferably 10° C.-50° C.

The time of hydrolysis is generally 1 hr-24 hr, preferably 1 hr-12 hr.

The compound obtained by hydrolysis is reacted with a calcium compound to give pitavastatin calcium. The compound obtained by hydrolysis is not necessarily isolated. Industrially, it is preferably hydrolyzed and continuously reacted with a calcium compound.

As the calcium compound, an inorganic salt or organic salt of calcium can be used, and calcium chloride, calcium acetate and the like can be preferably used.

A reaction temperature with a calcium compound lower than the boiling point of the solvent to be used and higher than the melting point of the solvent to be used hardly influences the reaction or the yield of the object product. Thus, the reaction temperature can be appropriately selected from this temperature range. Industrially, it is preferably 0° C.-70° C., more preferably 10° C.-60° C.

The reaction time is generally 0.1 hr-10 hr, preferably 0.5 hr-5 hr.

The method of filtration and drying of pitavastatin calcium is not particularly limited and a known method can be used.

The water content of pitavastatin calcium is generally 5 wt %-1.5 wt %, preferably 7 wt %-13 wt %, particularly preferably, 8 wt %-12 wt %. The obtained pitavastatin calcium may be adjusted to a desired water content by drying, or moistened after drying to adjust to a desired water content.

Step (iv):

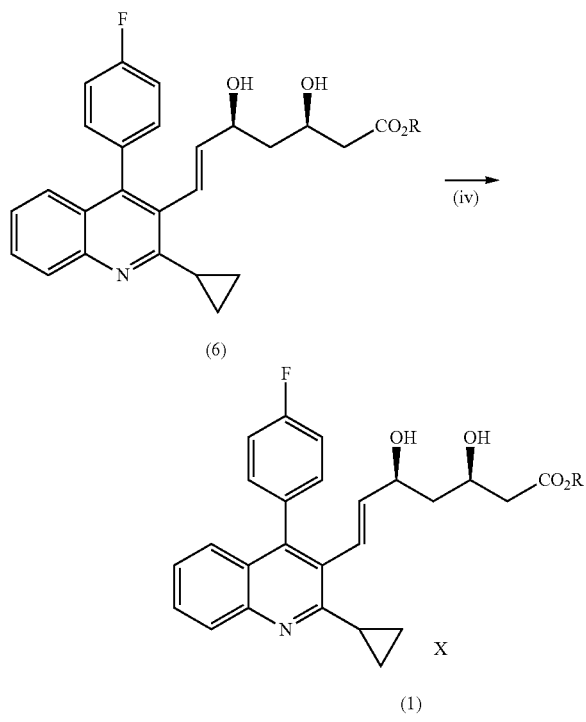

In step (iv), a compound represented by the formula (1) used in step (i) is obtained. To be specific, a compound represented by the formula (6) is reacted with an acid to give a compound represented by the formula (I).

A compound represented by the formula (1) is a salt of a compound represented by the formula (6). Preferred is a salt with mineral acid such as sulfate, hydrochloride and the like; a salt with organic acid such as formate, acetate, methanesulfonate, p-toluenesulfonate and the like, more preferably, sulfate, hydrochloride, methanesulfonate or p-toluenesulfonate. From the aspect of crystallinity, a compound represented by the formula (1) is industrially preferably methanesulfonate, namely, a compound represented by the following formula (1'):

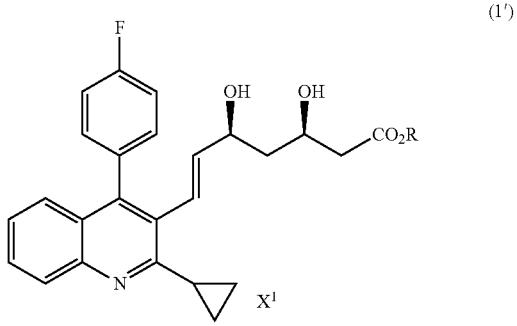

wherein $X^1$ is methanesulfonic acid and R is as defined above.

As the acid, mineral acids such as sulfuric acid, hydrochloric acid and the like; and organic acids such as formic acid, acetic acid, methanesulfonic acid, p-toluenesulfonic acid and the like can be used. One kind of these may be used or a mixture of two or more kinds thereof may also be used. Of these, sulfuric acid, hydrochloric acid, methanesulfonic acid or p-toluenesulfonic acid is industrially preferable.

The amount of the acid to be used is not particularly limited, and it is generally 1 mol-2 mol, preferably 1 mol-1.5 mol, relative to 1 mol of a compound represented by the formula (6).

The reaction is preferably performed using a solvent. While the solvent is not particularly limited as long as the reaction proceeds, hydrocarbon solvents such as cyclohexane, n-hexane, n-heptane, toluene and the like; ether solvents such as tert-butyl methyl ether, tetrahydrofuran (THF), cyclopentyl methyl ether (CPME) and the like; ester solvents such as ethyl acetate, propyl acetate, butyl acetate and the like; alcohol solvents such as methanol, ethanol, and the like; ketone solvents such as acetone, methylethyl ketone and the like; acetonitrile and the like are preferably used. One kind of these solvents may be used or a mixture of two or more kinds thereof may also be used.

The amount of the solvent to be used is not particularly limited, and it is generally 1 mL-100 mL, preferably 1 mL-50 mL, relative to 1 g of a compound represented by the formula (6).

A reaction temperature lower than the boiling point of the solvent to be used and higher than the melting point of the solvent to be used hardly influences the reaction or the yield of the object product. Thus, the reaction temperature can be appropriately selected from this temperature range. Industrially, it is preferably 0° C.-70° C., more preferably 10° C.-500.

The reaction time is generally 0.1 hr-10 hr, preferably 0.5 hr-5 hr.

A compound represented by the formula (6) sometimes contains impurity derived from the steps for obtaining the compound. For example, when a compound represented by the formula (6) is obtained by a bioreaction step such as the method of the below-mentioned (a) or (b), the resultant reaction product contains impurity besides a compound represented by the formula (6). Therefore, it is preferable to remove the impurity by purification and the like and use the compound in step (i).

A compound represented by the formula (1) obtained by step (iv) of the present invention, particularly methanesulfonate, is superior in crystallinity. Thus, it is easily precipitated as a crystal. Therefore, a compound represented by the formula (1) can be easily isolated.

The present invention having step (iv) can efficiently remove impurity from the previous step. Thus, a purification step can be omitted or simplified in the production on an industrial scale.

A compound represented by the formula (6) can be obtained so by an organic synthesis step or bioreaction step. In the present invention, a compound represented by the formula (6) is preferably produced by a method of the following (a) or (b)

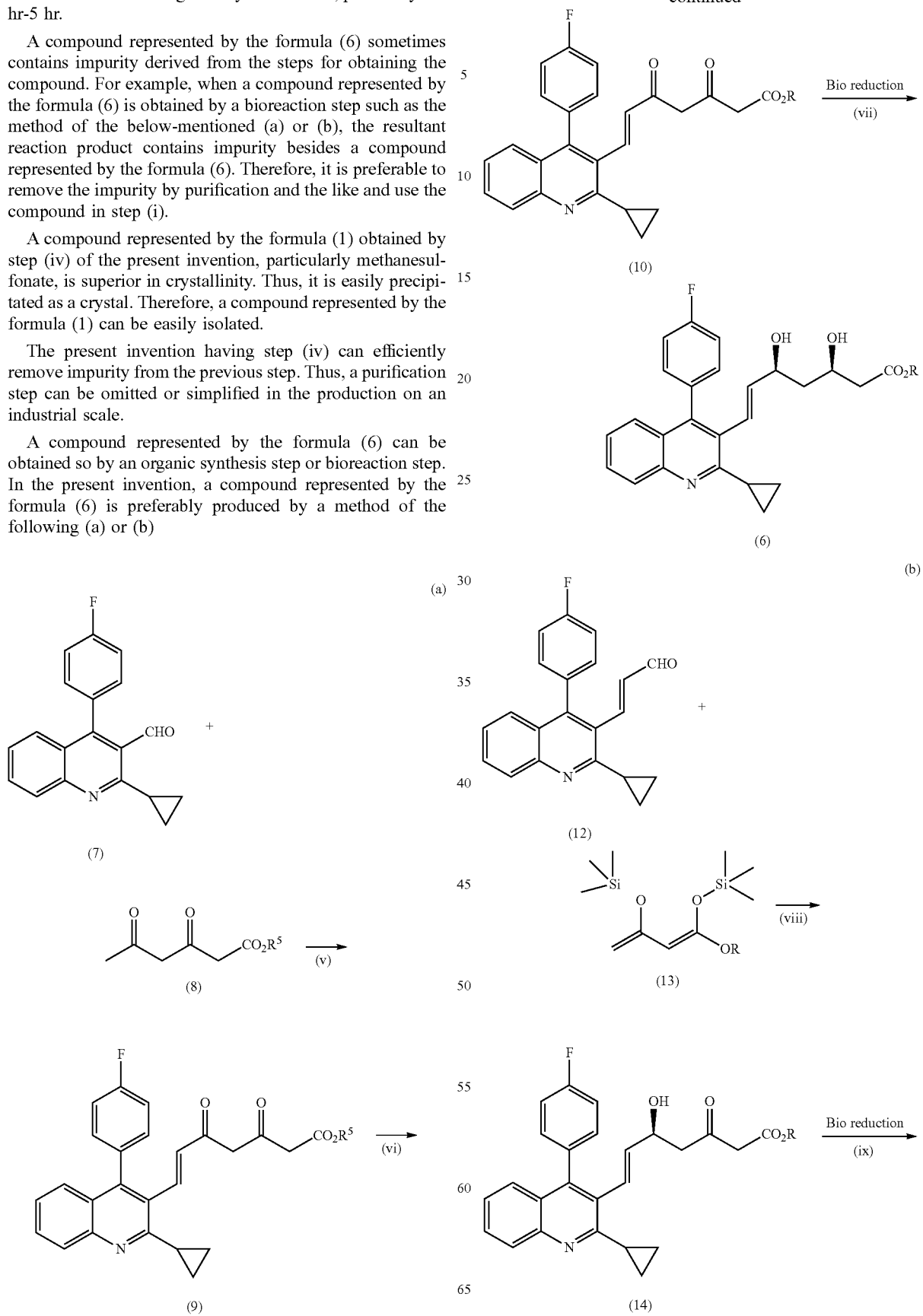

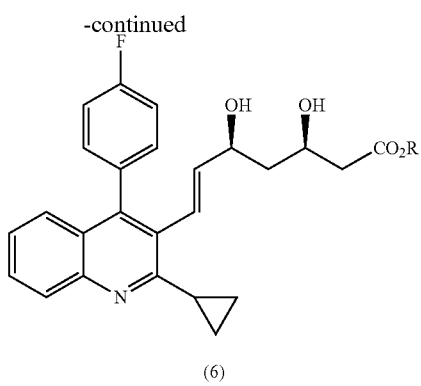

(6)

Method (a):

Method (a) characteristically includes step (v) step (vi) and step (vii).

Step (v)

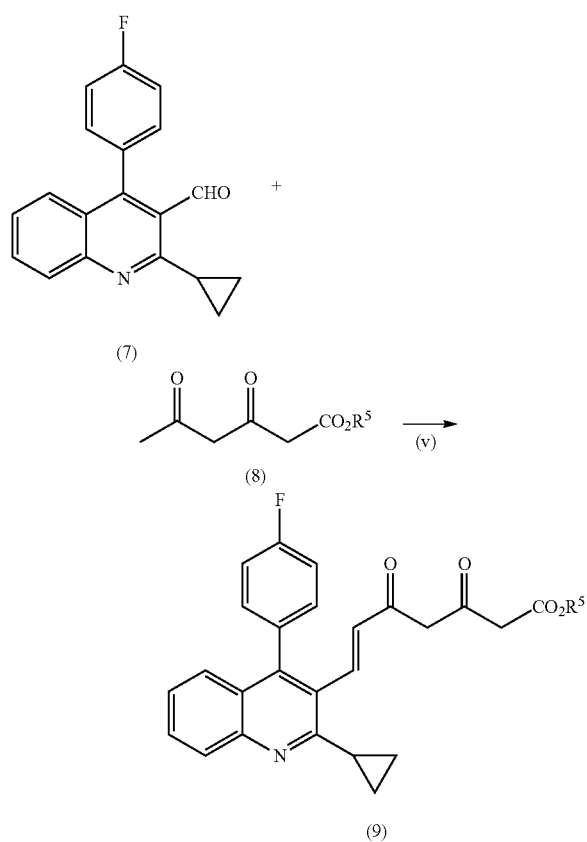

In step (v), a compound represented by the formula (7) and a compound represented by the formula (8) are condensed in the presence of a base to give a compound represented, by the formula (9).

As the base, metal hydrides such as sodium hydride, potassium hydride, calcium hydride and the like, metal amides such as sodium amide and the like, organic lithiums such as butyllithium, lithium diisopropylamide and the like, Grignard reagents such as tert-butylmagnesium chloride and the like, alkoxides such as sodium ethoxide, sodium tert-butoxide, potassium tert-butoxide and the like, and the like can be used. Particularly, sodium amide, sodium tert-butoxide and sodium hydride are preferable.

The amount of the base to be used is not particularly limited, and it is generally 1 mol-5 mol, preferably 1 mol-4 mol, relative to 1 mol of a compound represented, by the formula (7).

The condensation reaction can be performed using a solvent. While the solvent is not particularly limited as long as the reaction proceeds, hydrocarbon solvents such as cyclohexane, n-hexane, n-heptane, toluene and the like, halogenated solvents such as chlorobenzene, dichlorobenzene and the like, ether solvents such as tert-butyl methyl ether, tetrahydrofuran (THF), cyclopentyl methyl ether (CPME) and the like, polar solvents such as N-methyl-2-pyrrolidone, N,N-dimethylformamide, N, N-dimethylacetamide, dimethyl sulfoxide and the like, and the like can be used. One kind of these may be used or a mixture of two or more kinds thereof may also be used.

While the amount of the solvent to be used is not particularly limited, and it is generally 5 mL-100 mL, preferably 5 mL-30 mL, relative to 1 g of a compound represented by the formula (7).

A reaction temperature lower than the boiling point of the solvent to be used and higher than the melting point of the solvent to be used hardly influences the condensation reaction or the yield of the object product. Thus, the reaction temperature can be appropriately selected from this temperature range. Industrially, it is generally 0° C.-100° C., preferably 0° C.-50° C.

The reaction time is generally 0.1 hr-200 hr, preferably 1 hr-24 hr.

A compound represented by the formula (7) can be produced by the method described in, for example, JP-B-2569746, and a commercially available can also be used.

A compound represented by the formula (8) can be obtained according to a known method. For example, it can be obtained by the method described in SYNTHETIC COMMUNICATIONS, 18(7), 735-739 (1988). A commercially available compound can also be used.

A compound represented by the formula (8) has a pH of preferably not more than 4, more preferably not more than 3. By setting the pH of a compound represented by the formula (8) to fall within this range, the preservation stability of a compound represented by the formula (8) is improved, and formation of impurity during the reaction can be reduced. The pH of a compound represented by the formula (8) is a value obtained by mixing a compound represented by the formula (8) and water at 1:1 (volume ratio), and measuring the pH of the aqueous layer. When the pH value is too high (e.g., pH higher than 4), it can be lowered as necessary with an acid such as acetic acid, hydrochloric acid, sulfuric acid and the like.

From the aspect of crystallinity, $R^5$ in the formula (9) is preferably a branched alkyl group having a carbon number of 3-8, more preferably an isopropyl group, an s-butyl group, a tert-butyl group, a tert-amyl group, particularly preferably a tert-butyl group. A compound represented by the formula (9) having high crystallinity is industrially preferable because it can be obtained with high purity without complicated purification such as chromatography and the like.

Step (vi):

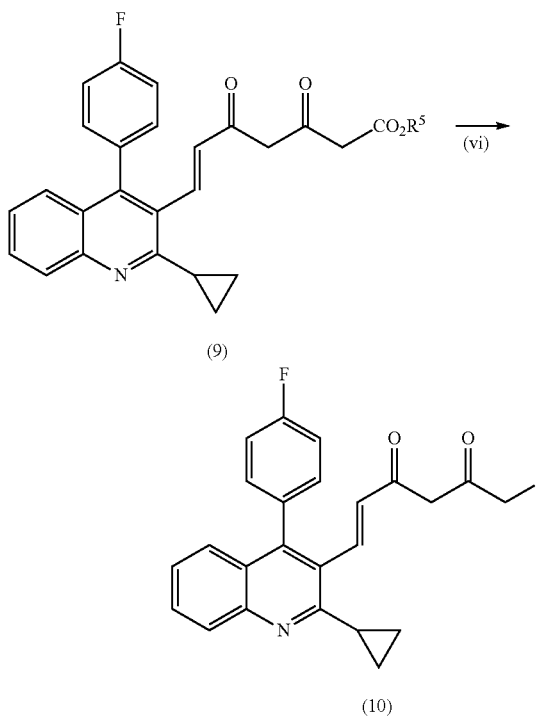

In step (vi), a compound represented by the formula (9) is reacted with alcohol represented by R—OH to give a compound represented by the formula (10).

The amount of alcohol represented by R—OH to be used is not particularly limited, and it is generally 1 mL-100 mL, preferably 1 mL-10 mL, relative to 1 g of a compound represented by the formula (9).

The reaction can be performed using a solvent. While the solvent is not particularly limited as long as the reaction proceeds, ester solvents such as ethyl acetate, methyl acetate, isopropyl acetate and the like; non-polar solvents such as cyclohexane, n-hexane, n-heptane, toluene and the like; halogen solvents such as methylene chloride, chloroform, carbon tetrachloride and the like; ether solvents such as tert-butyl methyl ether (MTBE), tetrahydrofuran (THF), cyclopentyl methyl ether (CPME) and the like; polar solvents such as N-methyl-2-pyrrolidone, N,N-dimethylformamide, N,N-dimethylacetamide, dimethyl sulfoxide and the like, and the like can be used. One kind of these may be used or a mixture of two or more kinds thereof can also be used. In addition, alcohol itself represented by R—OH may also be used as a solvent.

While the amount of the solvent to be used is not particularly limited, and it is generally 1 mL-100 ml, preferably 1 mL-10 ml, relative to 1 g of a compound represented by the formula (9).

A reaction temperature lower than the boiling point of the solvent to be used and higher than the melting point of the solvent to be used hardly influences the reaction or the yield of the object product. Thus, the reaction temperature can be appropriately selected from this temperature range. Industrially, it is generally 30° C.-150° C., preferably 40° C.-110° C.

The reaction time is generally 1 hr-48 hr, preferably 2 hr-24 hr.

From the aspect of reaction efficiency in bioreaction step (vii), R in R—OH and the formula (10) is preferably a straight chain alkyl group having a carbon number of 1-8, more preferably a straight chain alkyl group having a carbon 0.35 number of 1-4, particularly preferably a methyl group, an ethyl group or an n-propyl group. Such compound represented by the formula (10) is preferable since stereoselective reduction of carbonyl group proceeds efficiently in bioreaction step (vii).

Step (vii): bioreaction step

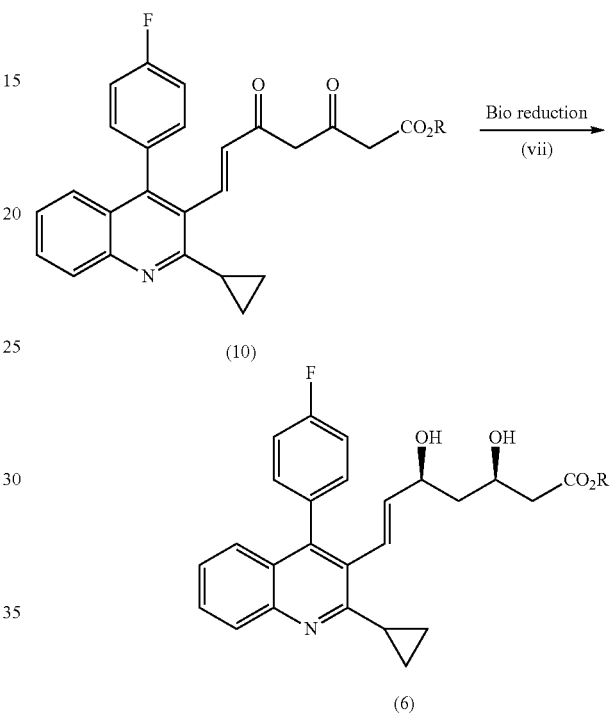

In step (vii), a compound represented by the formula (10) is reduced by reaction with an enzyme having an activity capable of stereoselectively reducing a carbonyl group, a microorganism or cell having an ability to produce the enzyme (the microorganism or cell of the present invention), a treated product of the microorganism or cell, and/or a culture medium containing the enzyme obtained by culturing the microorganism or cell (hereinafter these are sometimes collectively referred to as "the enzyme etc. of the present invention") to give a compound represented by the formula (6).

As the enzyme used in step (vii), one having the amino acid sequence shown in SEQ ID NO: 2 (hereinafter sometimes to be referred to as "OCR1") or a homologue of the amino acid sequence can be used. Specifically, an enzyme containing a polypeptide of the following (A), (B) or (C) or a homologue of these can be mentioned.

(A) a polypeptide having carbonyl reductase (OCR1) (SEQ ID NO: 2) derived from *Ogataea minuta* var. *nonfermentans* NBPC1473 described in JP-B-4270918, (B) a polypeptide consisting of an amino acid sequence having a homology of 80% or more to the amino acid sequence shown in SEQ so ID NO: 2, and having an activity to convert a compound represented by the formula (10) to a compound represented by the formula (6), (C) a polypeptide comprising an amino acid sequence which is the amino acid sequence shown in SEQ ID NO: 2, wherein 1 or several amino acids are substituted, deleted or added, and having an activity to convert a compound represented by the formula (10) to a compound represented by the formula (6).

A homologue of the above-mentioned (B) is a protein having at least 80%, preferably 85% or more, more preferably 90% or more, further preferably 95% or more, particularly preferably 98% or more, homology with the full-length amino acid sequence shown in SEQ ID NO: 2 as long as the activity to stereoselectively reduce carbonyl group is not impaired.

A homologue of the above-mentioned (C) has an amino acid sequence which is the amino acid sequence shown in SEQ ID NO: 2, wherein 1 or several amino acids are deleted, added or substituted, as long as the activity to stereoselectively reduce carbonyl group is not impaired. As used herein, "1 or several amino acids" is specifically 20 or less, preferably 10 or less, more preferably 5 or less, amino acids.

The gene encoding the above-mentioned enzyme is a DNA comprising the base sequence shown in the following (D), (E) or (F) or a homologue thereof:
(D) the base sequence shown in SEQ ID NO: 1,
(E) a base sequence that hybridizes to a DNA consisting of a sequence complementary to the base sequence shown in SEQ ID NO: 1 under stringent conditions, and encodes a polypeptide having an activity to act on a compound represented by the formula (10) and convert same to a compound represented by the formula (6),
(F) a base sequence having a base sequence which is the base sequence shown in SEQ ID NO: 1 wherein 1 or several bases are substituted, deleted or added, and encodes a polypeptide having an activity to act on a compound represented by the formula (10) and convert same to a compound represented by the formula (6).

Here, the "base sequence that hybridizes under stringent conditions" in the above-mentioned (E) means a base sequence of a DNA obtained by colony hybridization method, plaque hybridization method, or Southern blot hybridization method and the like under stringent conditions by using DNA as a probe. Examples of the stringent conditions in colony hybridization method and plaque hybridization method include conditions of hybridization using a filter immobilizing a colony- or plaque-derived DNA or a fragment of the DNA in the presence of a 0.7 mol/L-1.0 mol/L aqueous sodium chloride solution at 65° C., and washing the filter with 0.1-2×SSC solution (composition of 1×SSC, 150 rmol/L aqueous sodium chloride solution, 15 mmol/L aqueous sodium citrate solution) at 65° C.

Each hybridization can be performed according to the method described in Molecular Cloning: A Laboratory Manual, 2nd Ed., Cold Spring Harbor Laboratory, Cold Spring Harbor, N.Y., 1989 and the like.

A homologue of the above-mentioned (F) has a base sequence which is the base sequence shown in SEQ ID NO: 1, wherein 1 or several bases are deleted, added or substituted, as long as the activity to stereoselectively reduce carbonyl group is not impaired. As used herein, "1 or several bases" is specifically 60 or less, preferably 30 or less, more preferably or less, further preferably 10 or less, particularly preferably 5 or less, bases.

In step (vii), since the enzyme etc. of the present invention is superior in the handling property, and easily added to a reaction system, it can also be used in a frozen state. When frozen enzyme etc. of the present invention are used, the shape thereof is not particularly limited and, for example, prismatic, cylindrical, bulk, spherical shape and the like can be employed.

In step (vii), a compound represented by the formula (10) to be a reactant is generally used at a substrate concentration of 0.01% w/v-20% w/v, preferably 0.1% w/v-10% w/v. A reactant may be present in the reaction system in advance, or added at once at the start of the reaction. When the substrate is inhibited by the enzyme, the enzyme can also be added continuously or intermittently from the start of the reaction to reduce the influence thereof or improve accumulation concentration of the resultant product.

Step (vii) is preferably performed in the presence of coenzyme NAD(P)$^+$ or NAD(P)H. In this case, the above-mentioned coenzyme is preferably added at a concentration of generally 0.001 mmol/L-100 mmol/L, preferably 0.01 mmol/L-10 mmol/L.

When the above-mentioned coenzyme is added, regeneration of NAD(P)$^+$ produced from NAD(P)H into NAD(P)H in the reaction system is preferable in view of reaction efficiency. Examples of the regeneration method include
1) a method utilizing an ability to generate NAD(P)H from NAD(P)$^+$ of the microorganism or cell itself of the present invention, i.e., NAD (P)$^+$ reduction ability,
2) a method comprising addition of one or more kinds from a microorganism or a treated product thereof having an ability to generate NAD(P)H from NAD(P)$^+$, or an enzyme utilizable for regeneration of NAD(P)H such as glucose dehydrogenase, formate dehydrogenase, alcohol dehydrogenase, amino acid dehydrogenase, Jo organic acid dehydrogenase (malic acid dehydrogenase and the like) and the like (hereinafter to be referred to as "regenerating enzyme") to a reaction system,
3) a method comprising concurrent introduction of one or more kinds of the above-mentioned regenerating enzyme gene into a host organism or host cell when producing the microorganism or cell of the present invention, and the like.

In the above-mentioned method of 1), glucose, ethanol, 2-propanol or formic acid and the like are preferably added to the reaction system from the aspect of production efficiency.

In the above-mentioned method of 2), a microorganism having an ability to produce the above-mentioned regenerating enzyme, a treated product of microorganism such as the microorganism treated with acetone, glutaraldehyde-treated, or freeze-dry treated, physically or enzymatically disrupted and the like, the enzyme fraction obtained as a crude product or purified product, and further, these after immobilization on a carriers such as polyacrylamide gel, carageenan gel and the like, and the like may be used, or a commercially available enzyme may also be used.

The amount of the above-mentioned regenerating enzyme to be used is preferably such amount that renders the enzyme activity generally 0.01-fold to 100-fold, preferably about 0.5-fold to 20-fold, as compared to the carbonyl reduction activity of the enzyme of the present invention having an ability to stereoselectively reduce a carbonyl group.

While addition of a compound to be the substrate of the above-mentioned regenerating enzyme, for example, glucose when glucose dehydrogenase is utilized, formic acid when formate dehydrogenase is utilized, ethanol or isopropanol when alcohol dehydrogenase is utilized and the like, is also necessary, the amount thereof to be added is generally 0.1 mol-20 mol, preferably 1 equivalent-10 mol, relative to 1 mol of a compound represented by the formula (10).

In the method of the above-mentioned 3), a method for incorporating a DNA of the above-mentioned regenerating enzyme into chromosome along with a DNA encoding the enzyme used in step (i), a method for introducing both DNAs into a single expression vector and transforming a host organism or cell, or a method for introducing both DNAs into separate expression vectors and transforming a host organism or cell and the like can be used. In the method for introducing both DNAs into separate expression vectors, and transforming a host organism or cell, an expression vector needs to be selected in consideration of the incompatibility between both expression vectors.

When plural genes are introduced into a single expression vector, a method of connecting regions involved in the control of expression such as a promoter and a terminator and the like to each gene, and expression as an operon containing multiple cistrons such as lactose operon are also possible.

Step (vii) is performed in an aqueous medium or a mixture of an aqueous medium and an organic solvent. The aqueous medium or a mixture of an aqueous medium and an organic solvent contains a compound represented by the formula (10) and the above-mentioned enzyme, a microorganism or cell having an ability to produce the enzyme, a treated product of the microorganism or cell, and/or a culture medium containing the enzyme obtained by culturing the microorganism or cell. In addition, where necessary, various coenzymes may be contained. When a coenzyme is contained, a regenerating system thereof is more preferable, i.e., more preferably the coenzyme can be regenerated.

A compound represented by the formula (10) can also be produced by the below-mentioned method.

As the aqueous medium, water and pH buffers such as potassium phosphate buffer, sodium citrate buffer, Tris-HCl buffer and the like can be mentioned.

As the organic solvent, a solvent in which a compound represented by the formula (10) shows high solubility, such as ethyl acetate, isopropyl acetate, butyl acetate, toluene, chloroform, n-hexane, n-heptane, dimethyl sulfoxide, methanol, ethanol, n-propanol, 2-propanol and the like can be used. Of these, dimethyl sulfoxide, methanol, ethanol are preferable as an organic solvent, since a compound represented by the formula (10) shows high solubility therein. Furthermore, dimethyl sulfoxide is more preferable since conversion ratio is high.

Step (vii) is generally performed at a reaction temperature of 4° C.-70° C., preferably 30° C.-60° C., generally at pH 3-11, preferably pH 4-8. The reaction time is generally 0.5 hr-48 hr, preferably 0.5 hr-24 hr.

A compound represented by the formula (6) obtained in step (vii) can be purified by separating bacterial cells, polypeptide and the like by centrifugation, filtration and the like, adjusting to a suitable pH, and applying an appropriate combination of extraction with an organic solvent such as hexane, ethyl acetate, toluene and the like, and purification by column chromatography, crystallization and the like.

Method (b):

Method (b) characteristically includes step (viii) and step (ix).

Step (viii):

(12)

In step (viii), a compound represented by the formula (12) is reacted with a compound represented by the formula (13) in the presence of a titanium catalyst (Ti catalyst) represented by the following formula (15) to give a compound represented by the formula (14).

(15)

wherein Ra is an alkyl group having a carbon number of 1-10.

The amount of a compound represented by the formula (13) to be used is not particularly limited, and it is generally 1 mol-10 mol, preferably 1 mol-5 mol, relative to 1 mol of a compound represented by the formula (12).

The binaphthyl structure of the Ti catalyst represented by the formula (15) is preferably an S conformation. As Ra, a lower alkyl group having a carbon number of 1-4 such as a methyl group, an ethyl group, a propyl group, an isopropyl group, a butyl group, a t-butyl group or the like is preferable, and industrially, an isopropyl group is particularly preferable.

The amount of the Ti catalyst to be used is not particularly limited, and it is generally 0.001 mol-1 mol, preferably 0.01 mol-0.5 mol, relative to 1 mol of a compound represented by the formula (12).

The reaction is preferably performed using a solvent. While the solvent is not particularly limited as long as the reaction proceeds, hydrocarbon solvents such as cyclohexane, n-hexane, n-heptane, toluene and the like; ether solvents such as tert-butyl methyl ether, tetrahydrofuran (THF), cyclopentyl methyl ether (CPME) and the like; ester solvents such as ethyl acetate, propyl acetate, butyl acetate and the like; acetonitrile and the like are preferably used.

One kind of these solvents may be used or a mixture of two or more kinds thereof may also be used.

The amount of the solvent to be used is not particularly limited, and it is generally 1 mL-100 mL, preferably 1 mL-50 mL, relative to 1 g of a compound represented by the formula (12).

It is also possible to add lithium chloride and/or synthetic zeolite to the reaction system. As a result, a desired one with a high optical purity can be obtained.

The amount of the lithium chloride to be used is not particularly limited, and it is generally 0.001 mol-2 mol, preferably 0.01 mol-1 mol, relative to 1 mol of a compound represented by the formula (12).

Examples of the synthetic zeolite include molecular sieves 3A, 4A, 5A, 13X and the like, preferably, molecular sieves 3A, 4A.

The amount of the synthetic zeolite to be used is not particularly limited, and it is generally 0.01-1 g, preferably 0.1-0.5 g, relative to 1 g of a compound represented by the formula (12).

A reaction temperature lower than the boiling point of the solvent to be used and higher than the melting point of the solvent to be used hardly influences the reaction or the yield of the object product. Thus, the reaction temperature can be appropriately selected from this temperature range. Industrially, it is preferably 0° C.-100° C., more preferably 10° C.-50° C.

The reaction time is generally 1 hr-24 hr, preferably 1 hr-12 hr.

A compound represented by the formula (12) can be obtained according to a known method. For example, it can be obtained by the method described in WO 2000/42016. In addition, a commercially available one can also be used.

A compound represented by the formula (13) can also be obtained according to a known method as shown below. For example, it can be obtained by the method described in WO 2003/420180.

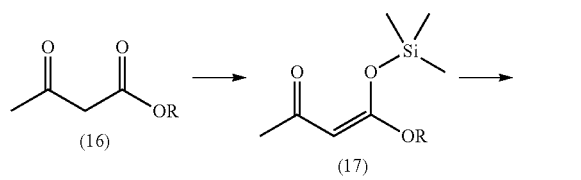

(16) → (17)

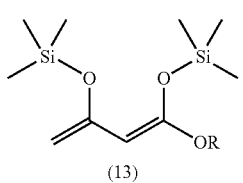

(13)

Step (ix):

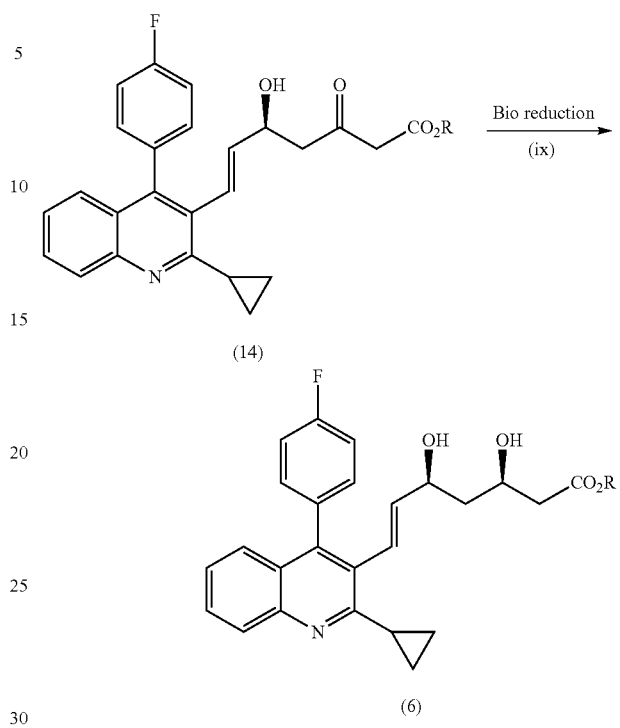

In step (ix), a compound represented by the formula (14) is reduced by reaction with an enzyme having an activity capable of stereoselectively reducing a carbonyl group, a microorganism or cell having an ability to produce the enzyme (the microorganism or cell of the present invention), a treated product of the microorganism or cell, and/or a culture medium containing the enzyme obtained by culturing the microorganism or cell to give a compound represented by the formula (6).

Step (ix) can be performed in the same manner as in the aforementioned step (vii).

EXAMPLES

The present invention is further explained in detail in the following by referring to Examples; however, the present invention is not limited by the Examples.

The abbreviations in the Examples show the following compounds.

PT-DOXE: (6E)-7-[2-cyclopropyl-4-(4-fluorophenyl)-3-quinolinyl]-3,5-dioxo-6-heptenoic acid ethyl ester
PT-ALD: [2-cyclopropyl-4-(4-fluorophenyl)-3-quinolinyl] carbaldehyde
DHAB: 3,5-dioxoheptenoic acid t-butyl ester
PT-DOXB: (6E)-7-[2-cyclopropyl-4-(4-fluorophenyl)-3-quinolinyl]-3,5-dioxo-6-heptenoic acid t-butyl ester
PT-DOLE: (3R,5S,6E)-7-[2-cyclopropyl-4-(4-fluorophenyl)-3-quinolinyl]-3,5-dihydroxy-6-heptenoic acid ethyl ester
DOLE MsOH: (3R,5S,6E)-7-[2-cyclopropyl-4-(4-fluorophenyl)-3-quinolinyl]-3,5-dihydroxy-6-heptenoic acid ethyl ester methanesulfonate
5S-MOLE: (E-(5S)-7-[2-cyclopropyl-4-(4-fluorophenyl)-quinolin-3-yl]-5-hydroxy-3-oxo-hept-6-enoic acid ethyl ester
ACPT: (4R,6S,1E)-2-[2-cyclopropyl-4-(4-fluorophenyl)-3-quinolinyl]-2,2-dimethyl-, 3-dioxolan-4-acetic acid ethyl ester Me: methyl group
Et: ethyl group
t-Bu: tertiary butyl group
EtOH: ethanol
THF: tetrahydrofuran
DMF: N, N-dimethylformamide The assay analysis in the Examples included measurement under the following conditions by using HPLC (High Performance Liquid Chromatography)

<Chemical Purity of PT-DOXE>
Column: Capcell Pak C18 MG (4.6 mm×75 mm, 3 μm) manufactured by Shiseido Co., Ltd.
Mobile phase:
A: water/acetic acid/ammonium acetate=1000/100/7.7 (mL/mL/g)
B: THF
Gradient program (B concentration): 41 vol % (0 min)→41 vol % (17 min)→90 vol % (27 min)
Flow rate: 1 mL/min
Column temperature: 40° C.
Detection wavelength: UV 254 nm <Chemical Purity of PT-DOLE>
Column: L-Column ODS (4.6 mm×250 mm, 5 μm) manufactured by CERI
Mobile phase:
A: 10 mmol/L ammonium acetate
B: ethanol/THF=15/1 (volume ratio)
Gradient program (B concentration): 48 vol % (0 min)→48 vol % (35 min)→64 vol % (55 min)
Flow rate: 1.0 mL/min
Column temperature: 40° C.
Detection wavelength: UV 245 nm <Chemical Purity of ACPT>
Column: Unison UK-C18 (4.6 mm×250 mm, 3 μm) manufactured by Imtact
Mobile phase:
A: 30 mmol/L aqueous ammonium acetate solution/acetonitrile=20/80 (volume ratio)
B: 30 mmol/L aqueous ammonium acetate solution/acetonitrile=5/95 (volume ratio)
Gradient program (B concentration): 0 vol % (0 min)→0 vol % (10 min)-90 vol % (30 min)
Flow rate: 1 mL/min
Column temperature: 40° C.
Detection wavelength: UV 245 nm <Chemical Purity of Pitavastatin Calcium>
Column: Unison UK-C18 (4.6 mm×250 mm, 3 μm) manufactured by Imtact
Mobile phase:
A: 0.1 vol % formic acid
B: acetonitrile
Gradient program (B concentration): 25 vol % (0 min)→35 vol % (20 min)→90 vol % (30 min)→90 vol % (35 min)
Flow rate: 1 mL/min
Column temperature: 40° C.
Detection wavelength: UV 331 nm <Measurement Condition of Powder X-Ray Diffraction>
Measuring apparatus: type XRD6000 manufactured by SHIMADZU Corporation
Radiation source: Cu
Wavelength: 1.54060 Å
Monochromator: used
Tube voltage: 40.0 Kv
Tube current: 40.0 mA
Divergence: 1.00 deg
Scattering: 1.00 deg
Receiving: 0.15 mm
Mode: continuous scan
Driving shaft: θ-2θ
Data range: 2-40 deg
Step: 0.02 deg
Scan speed: 2.0000 deg/min
Rotating speed: 60 rpm Example 1 (Production of PT-DOXE)

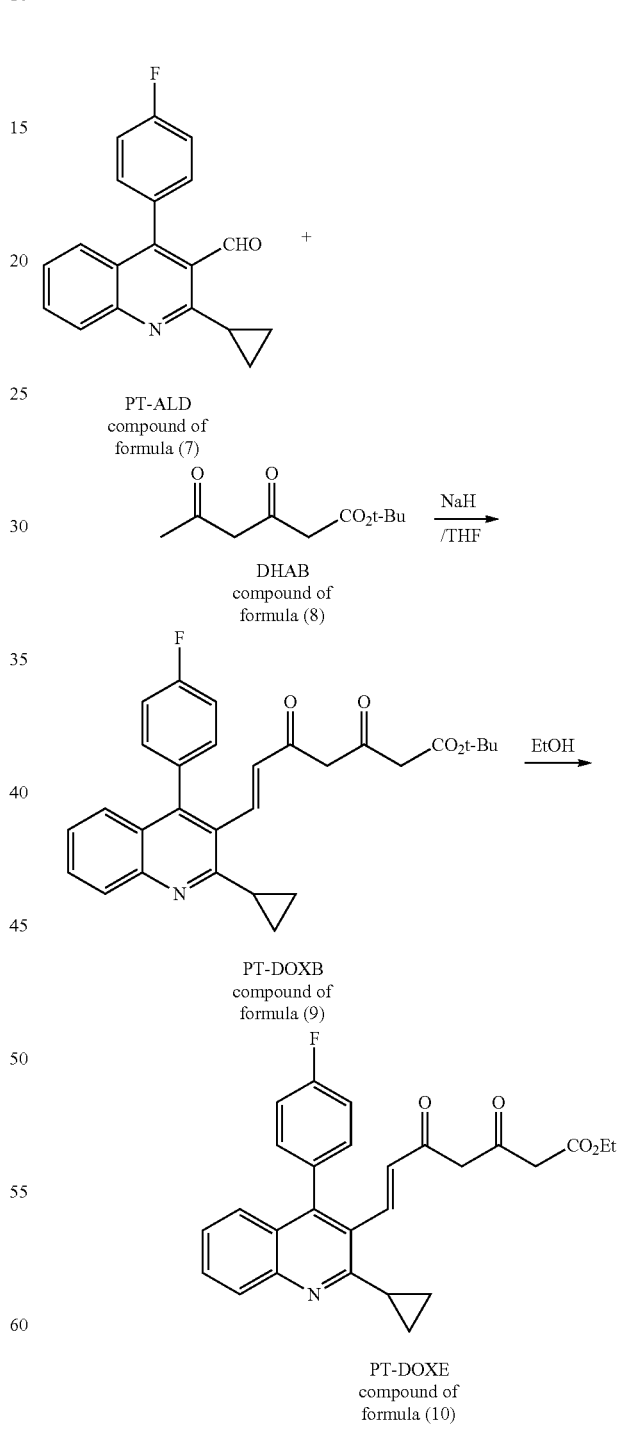

Under a nitrogen atmosphere, sodium hydride (20.8 g, purity 59.5%, 515 mmol) and THF (200 mL) were charged in a flask and cooled to 17° C. To this mixture was added dropwise a solution of DHAB (53.9 g, purity 91.9%, 247.1 mmol) in THF (200 mL) over 2 hr, and the solution after completion of the dropwise addition was stirred at 25° C. for 13 hr.

To the solution after stirring was added dropwise a solution of PT-ALD (40.0 g, 137.3 mmol) in THF (400 mL) over 4 hr, and the solution after completion of the dropwise addition was stirred at 25° C. for 1 hr. The solution after stirring was analyzed by HPLC to find that the conversion ratio to PT-DOXB was 99.2%.

To the solution after stirring were added dropwise n-heptane (200 mL) and water (400 mL) at 25° C. and partitioned. Thereafter, the organic layer was washed with 4 wt % aqueous sodium chloride solution, 10 wt % aqueous citric acid solution and 10 wt % aqueous sodium chloride solution. The obtained organic layer was analyzed by HPLC to find that the yield of PT-DOXB was 88.2%.

The obtained organic layer was concentrated under reduced pressure and ethanol (200 mL) was added. The obtained solution was heated in an autoclave (sealed vessel) to an inside temperature 100° C.-1050 and maintained. After 10 hr progress, the obtained solution was analyzed by HPLC to find that the conversion ratio to PT-DOXE was 99.0%. The obtained solution was cooled to 64° C. and stirred for 1 hr. The solution after stirring was gradually cooled to 0° C. to −5° C., and the crystal was recovered by filtration.

The obtained crystal and ethanol (200 ml) were charged in a flask and heated to a temperature at which ethanol is refluxed. Thereafter, the mixture was cooled to an inside temperature 70° C. and stirred for 1 hr. The solution after stirring was gradually cooled to 0° C. to −5° C., and the crystal was recovered by filtration and dried under reduced pressure. The obtained crystal was analyzed by HPLC to find that the purity of PT-DOXE was 99.1 area % and the quantity was 39.7 g (yield 64.9%).

Example 2 (Production of PT-DOXB)

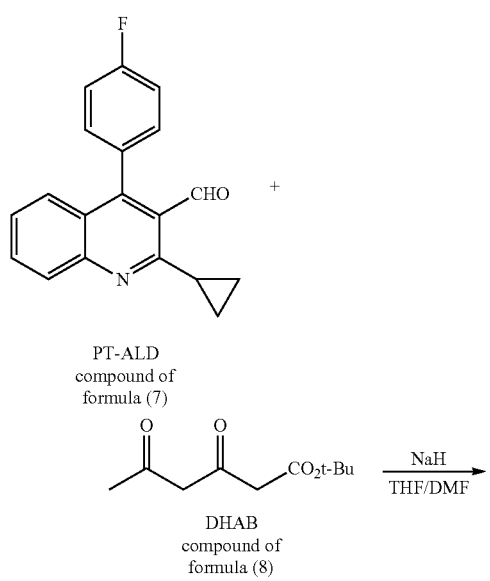

PT-ALD
compound of
formula (7)

DHAB
compound of
formula (8)

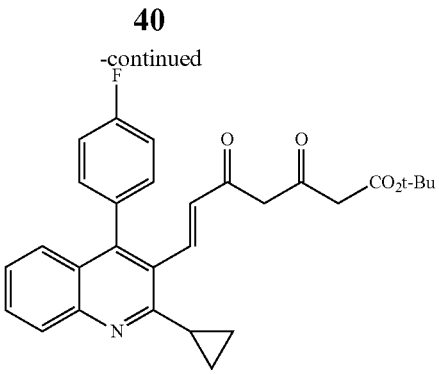

PT-DOXB
compound of
formula (9)

Under a nitrogen atmosphere, sodium hydride (15.6 g, purity 59.5%, 386 mmol), THF (150 mL) and N,N-dimethylformamide (75 mL) were charged in a flask and cooled to 5° C. To this mixture was added dropwise a solution of DHAB (40.4 g, purity 91.9%, 185.4 mmol) in THF (150 mL) over 2 hr, and the mixed solution after completion of the dropwise addition was stirred at 8 to 10° C. for 14 hr.

To the mixed solution after stirring was added dropwise a solution of PT-ALD (30.0 g, 103.0 mmol) in THF (225 mL) over 3 hr, and the solution after completion of the dropwise addition was stirred at 8 to 10° C. for 6 hr. The solution after stirring was analyzed by HPLC to find that the conversion ratio to PT-DOXB was 98.5%.

To the solution after stirring were added dropwise n-heptane (150 mL) and water (150 mL) at 10° C. and partitioned. Thereafter, the organic layer was washed with 4 wt % aqueous sodium chloride solution, 10 wt % aqueous citric acid solution and 10 wt % aqueous sodium chloride solution. The obtained organic layer was analyzed by HPLC to find that the yield of PT-DOXB was 88.9%.

Reference Example 1 (Preparation of Bacterial Cells)

[Preparation of Recombinant *Escherichia coli* 7M109/pKV320CR1-GDH Co-Expressing Carbonyl Reductase (Hereinafter OCR1) and Glucose-1-Dehydrogenase (Hereinafter GDH)]

(1) Cloning of Gene

Primers ocr1_F (SEQ ID NO: 3) and ocr1_R (SEQ ID NO: 4) for amplifying full-length ocr1 gene were designed and synthesized based on the gene sequence (ocr1) encoding OCR1 (SEQ ID NO: 2 described in JP-B-4270918) derived from *Ogataea minuta* variant *nonfermentans* (*Ogataea minuta* var. *nonfermentans*) NBRC (former IFO) 1473. Then, PCR was performed according to a conventional method and using chromosome DNA of *Ogataea*-Minuta variant *nonfermentans* (*Ogataea minuta* var. *nonfermentans*) as a template to give an about 0.8 kbp DNA fragment.

Then, based on a gene sequence (hereinafter gdh (SEQ ID NO: 5)) encoding GDH (SEQ ID NO: 6), which is glucose-1-dehydrogenase encoded by a gene (GeneBank Accession No. AL009126.3) derived from *Bacillus subtilis* (*Bacillus subtilis*) wherein glutamic acid, which is the 96th amino acid residue, is substituted by alanine, primer gdh_F1 (SEQ ID NO: 7) and gdh_R1 (SEQ ID NO: 8) for amplifying full-length gdh gene were designed and synthesized. Then, PCR was performed according to a conventional method to give an about 0.8 kbp DNA fragment.

(2) Preparation of Expression Plasmid

The DNA fragment of ocr1 obtained in the above-mentioned (1) was digested with restriction enzymes EcoRI and HindIII, and introduced into the downstream of trc promoter in the plasmid pKV32 (described in JP-A-2005-34025) and digested with MunI and HindIII, by using Ligation-Convenience Kit (manufactured by Nippon Gene Co., Ltd.) to give pKV32OCR1.

Then, the DNA fragment of gdh obtained in the above-mentioned (1) was digested with restriction enzymes EcoRI and XbaI, and introduced into the downstream of trc promoter in the plasmid pKV32 digested with MunI and XbaI, by using Ligation-Convenience Kit (manufactured by Nippon Gene Co., Ltd.) to give pKV32GDH.

Using pKV32GDH as a template and primers gdh_F2 (SEQ ID NO: 9) and gdh_R2 (SEQ ID NO: 10) added with restriction enzyme site HindIII, PCR was performed, and the obtained fragment was digested with restriction enzyme HindIII and inserted into the downstream of plasmid pKV32OCR1 digested with restriction enzyme HindIII in advance to give pKV32OCR1-GDH. The orientation of gdh gene in the obtained plasmid was confirmed by PCR.

(3) Preparation of Expression Strain

Using plasmid pKV32OCR1-GDH obtained in the above-mentioned (2), *Escherichia coli* JM109 (manufactured by TAKARA BIO INC.) was transformed according to a conventional method to give recombinant *Escherichia coli* JM109/pKV32OCR1-GDH.

Example 3 (Production of PT-DOLE)

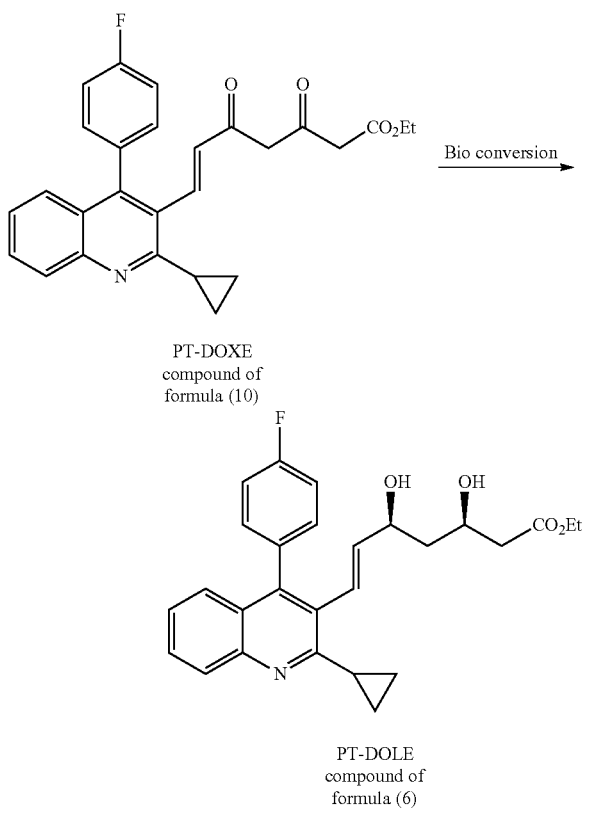

Ion exchange water (57 mL), glucose monohydrate (30 g, 151.5 mmol), NADP+ (30 mg, 0.04 mmol), potassium dihydrogen phosphate (2.76 g, 20.3 mmol) and dipotassium hydrogen phosphate (0.39 g, 2.3 mmol) were charged in a 250 mL jar fermentor and dissolved therein. Thereto were added frozen bacterial cells (45 g) of recombinant *Escherichia coli* JM109/pKV32OCR1-GDH prepared by the method of Reference Example 1 and the total amount of a substrate solution prepared by dissolving PT-DOXE (1.2 g, 2.69 mmol) obtained by a method similar to Example 1 in dimethyl sulfoxide (DMSO) (36.3 g), and the mixture was reacted by stirring at an inside temperature of 50° C. for 4 hr. During the reaction, 25 wt % aqueous sodium hydroxide solution was added dropwise to maintain pH 6. The obtained reaction mixture was diluted 36-fold with acetonitrile, filtered through a filter with pore size 0.2 nm and the filtrate was obtained. The filtrate was analyzed by HPLC to find that the conversion ratio from PT-DOXE to PT-DOLE was 85.7%.

Example 4 (Production of PT-DOLE)

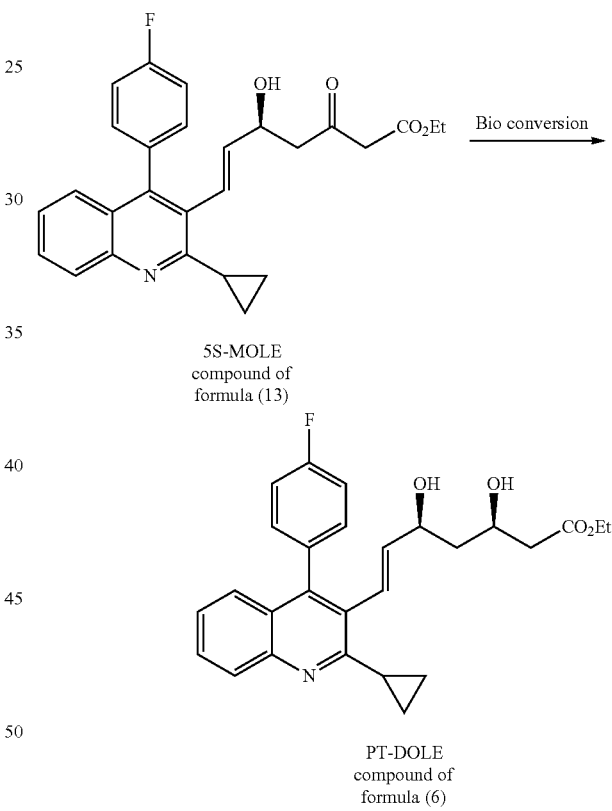

Ion exchange water (12 L), glucose monohydrate (750 g), NADP+ (2.9 g), dipotassium hydrogen phosphate (20.85 g, 0.12 mol) and potassium dihydrogen phosphate (147.0 g, 1.08 mol) were charged in a 30 L jar fermentor and dissolved therein. Thereto were added frozen bacterial, cells (2.1 kg) of recombinant *Escherichia coli* JM109/pKV32OCR1-GDH prepared by the method of Reference Example 1 and the total amount of a substrate solution prepared by dissolving 5S-MOLE (produced according to the method described in National Publication of International Patent Application No. 2005-516064) (0.3 kg, 0.67 mol) in dimethyl sulfoxide (DMSO) (3.3 kg), and the mixture was reacted by stirring at an inside temperature of 50° C. for 3 hr. During the reaction, 25 wt % aqueous sodium hydroxide solution was added dropwise to maintain pH 6.5. The obtained reaction mixture was centrifuged at 10,000 rpm for 10 min to give a precipitate consisting of bacterial cells and resultant reaction product. The precipitate was suspended in a 5 wt % aqueous sodium sulfate solution, and extracted with ethyl acetate. Extraction with ethyl acetate was repeated three times. The obtained extracts were combined to give a solution. The obtained solution was analyzed by HPLC to find that the purity of PT-DOLE was 97.6 area % and the yield was 236 g (yield 78.7%).

Example 5 (Production of DOLE MsOH)

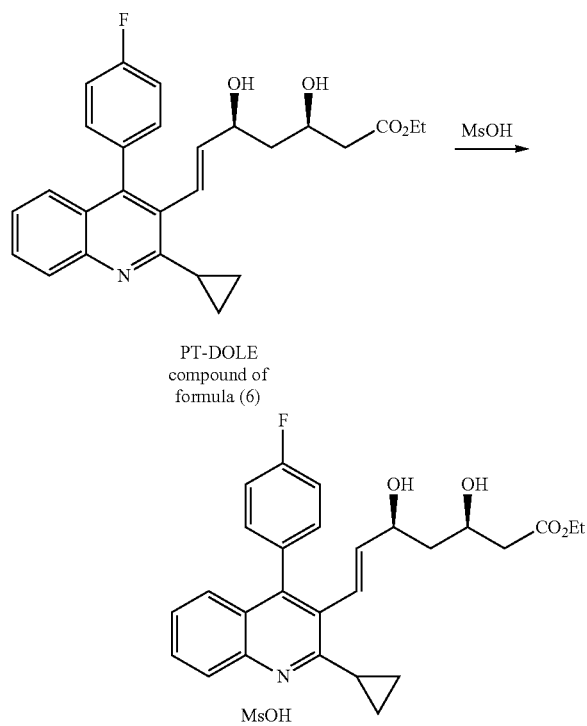

A solution of PT-DOLE obtained by a method similar to Example 4 was concentrated under reduced pressure, and a solution of PT-DOLE prepared to a concentration of 11.6 wt % was obtained. To the obtained PT-DOLE solution (377.6 g, 97.4 mmol) was added methanesulfonic acid (0.5 g, 5.2 mmol) at 30° C., and the mixture was stirred at the same temperature for 1.5 hr. A solution of methanesulfonic acid (8.9 g, 92.6 mmol) dissolved in ethyl acetate (39.3 g) was added dropwise. After completion of the dropwise addition, the reaction mixture was cooled to −3° C.

After cooling, the obtained slurry was filtered, and the residue was dried under reduced pressure at an outer temperature of 40° C. The obtained solid was analyzed by HPLC to find that the yield of DOLE MsOH was 52.4 g (yield 98%). The melting point, $^1$H-NMR and powder X-ray diffraction (XRD) measurement results of the obtained solid were as follows.

melting point: 132° C.

$^1$H-NMR (400 MHz, DMSO) δ 1.22-1.24 (6H, m), 1.46 (2H, s), 1.49 (1H, nm), 2.22-2.33 (2H, m), 2.37 (3H, s), 2.61 (1H, m), 3.76 (1H, m), 4.08 (2H, t, J=8 Hz), 4.14 (1H, m), 5.67 (1H, dd, J=4 Hz, 16 Hz), 6.53 (1H, d, J=16 Hz), 7.35-7.40 (5H, m), 7.56 (1H, m), 7.82 (1H, m), 8.09 (1H, m)

XRD measurement results:

TABLE 1

| 2θ | relative intensity |
|---|---|
| 6.9 | 20 |
| 13.5 | 28 |
| 15.3 | 9 |
| 15.7 | 5 |
| 16.5 | 6 |
| 17.0 | 14 |
| 18.8 | 13 |
| 19.8 | 9 |
| 20.6 | 100 |
| 21.1 | 16 |
| 21.8 | 42 |
| 22.2 | 16 |
| 23.9 | 11 |
| 24.5 | 7 |
| 24.7 | 8 |
| 25.0 | 10 |
| 26.2 | 8 |
| 26.9 | 6 |
| 27.8 | 9 |
| 28.2 | 9 |
| 29.6 | 7 |
| 29.8 | 6 |
| 30.1 | 5 |
| 30.6 | 5 |
| 30.9 | 8 |
| 33.0 | 5 |
| 33.6 | 7 |
| 34.2 | 5 |
| 34.6 | 5 |
| 34.8 | 5 |
| 35.6 | 5 |
| 39.0 | 5 |

Example 6 (Production of ACPT)

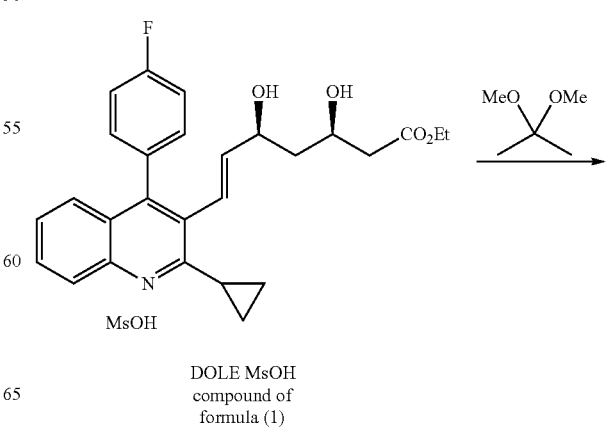

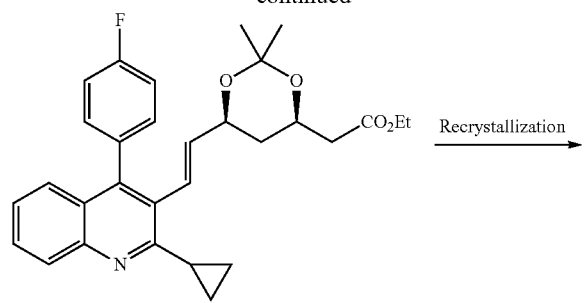

ACPT (crude crystal)
compound of
formula (3)

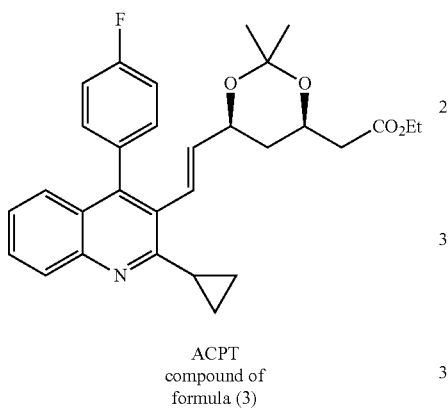

ACPT
compound of
formula (3)

DOLE MsOH (15.0 g, 27.5 mmol) obtained by a method similar to Example 5 and acetonitrile (58.5 g) were charged in a flask. To the mixture was added acetone dimethylacetal (11.3 g, 109 mmol) at an inside temperature of 20° C. After stirring for 3 hr, sodium hydrogen carbonate (2.9 g) and water (19.5 g) were added. Water (13.0 g) was further added and the mixture was stirred for 12 hr. Thereafter, water (42.2 g) was added, the inside temperature was cooled to −4° C., the obtained crystals were collected by filtration and dried under reduced pressure to give ACPT as crude crystals (13.3 g, yield 99%).

The crude crystal (10 g) of the obtained ACPT, ethanol (58.8 g) and water (14.7 g) were charged in a flask and dissolved by raising the inside temperature to around 60° C. The obtained solution was cooled to an inside temperature of around 37° C. and stirred for a while to precipitate crystals. Thereafter, the inside temperature was cooled to −3° C. over 6 hr. The obtained crystals were collected by filtration and dried under reduced pressure. The obtained crystals were analyzed by HPLC to find that the purity of ACPT was 99.8 area % and the yield was 8.9 g (yield 89%).

Example 7 (Production of Pitavastatin Calcium)

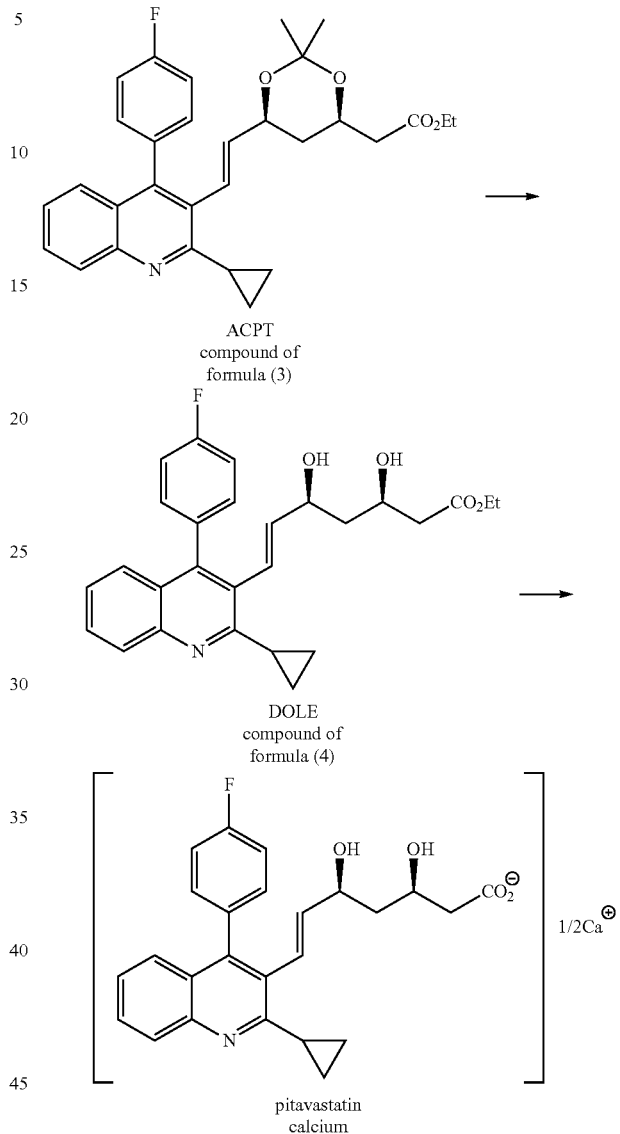

ACPT crystals (8 g, 16.3 mmol) obtained by a method similar to Example 6 and ethanol (40 mL) were charged in a so flask. To the mixture was added a mixed solution of 35 wt % hydrochloric acid (2.4 g) and water (21.6 g) at an inside temperature of around 30° C. After stirring for 3.5 hr, ethyl acetate (90 mL) and 7 wt % aqueous sodium hydrogen carbonate solution (45 g) were added. The obtained solution was partitioned, ethyl acetate (45 mL) was added to the aqueous layer and the mixture was partitioned. The obtained organic layers were combined, washed with 20 wt % aqueous sodium chloride solution (45 g) and concentrated.

After concentration, to the obtained residue were added ethanol (74 mL) and water (74 mL). To the mixture was added 8 wt % aqueous sodium hydroxide solution (9.9 g). After stirring for 3 hr, the obtained solution was concentrated under reduced pressure. After concentration under reduced pressure, to the obtained residue was added t-butyl methyl ether (37 mL) and the mixture was partitioned. This operation was performed twice. The aqueous layer was concentrated under reduced pressure, and a solution of calcium chloride 2 hydrate (2.6 g) dissolved in water (104 g) was added dropwise at an inside temperature of around 32° C. Thereafter, the obtained reaction mixture was cooled to around 2° C., the resulting crystals were collected by filtration and wet crystals were dried under reduced pressure. When the water content of the crystals reached 9.6 wt %, the drying was discontinued. The obtained crystals were analyzed by HPLC to find that the purity of pitavastatin calcium was 99.93 area % and the yield was 9.7 g (yield 94%).

Example 8 (Production of Pitavastatin Calcium)

ACPT crystals (70 g, 143 mmol) obtained by a method similar to Example 6 and ethanol (350 mL) were charged in a flask. To the mixture was added 3.5 wt % hydrochloric acid (208 g) at an inside temperature of around 30° C. After stirring for 2 hr, ethanol (210 mL) was added and 8 wt % aqueous sodium hydroxide solution (100 g) was added. The mixture was concentrated to a volume of 630 mL. Thereafter, 3.5 wt % hydrochloric acid (178 g) was added, and the mixture was stirred at room temperature for 2 hr. Thereafter, 8 wt % aqueous sodium hydroxide solution (178 g) was added, and the mixture was stirred at room temperature for 2 hr. To the mixture was added 210 mL of water, and the mixture was concentrated to a volume of 700 mL. To the concentrate were added water (350 mL) and t-butyl methyl ether (350 mL), the mixture was partitioned, and the aqueous layer was concentrated to a volume of 980 mL. To the obtained concentrate was added dropwise a mixed solution of calcium chloride 2 hydrate (22.9 g) and the water (173 g) at a temperature around 30° C. The obtained slurry was cooled to room temperature, the resulting crystals were collected by filtration and wet crystals were dried under reduced pressure. The water content of the obtained crystals was 7.8 wt %. Moistened nitrogen was flown through the obtained crystals to adjust the water content to 10.9 wt %. The obtained crystals were analyzed by HPLC to find that the purity of pitavastatin calcium was 99.96 area % and the yield was 66.0 g (yield 93%).

INDUSTRIAL APPLICABILITY

According to the method of the present invention, pitavastatin calcium can be safely produced on an industrial scale in a high yield with high selectivity at a low cost.

This application is based on patent application No. 2015-154864 filed in Japan, the contents of which are encompassed in full herein.

The invention claimed is:

1. A method for producing pitavastatin calcium comprising
   (i) acetalizing a compound represented by the following formula (1):

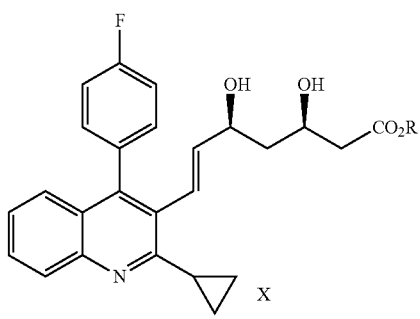

wherein R is a straight chain alkyl group having a carbon number of 1-8 or a branched alkyl group having a carbon number of 3-8 and X is an acid, to give a compound represented by the following formula (3):

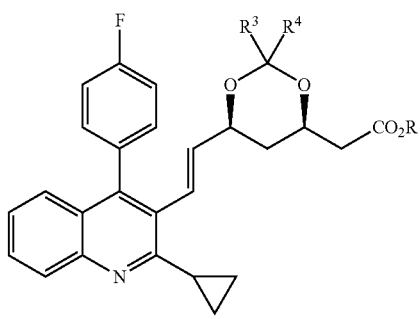

wherein $R^3$ and $R^4$ are each independently an alkyl group having a carbon number of 1-4 and R is as defined above;
   (ii) reacting said compound represented by the formula (3) with an acid to give a compound represented by the following formula (4):

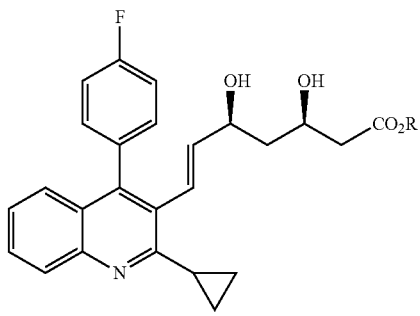

wherein R is as defined above; and
   (iii) hydrolyzing said compound represented by the formula (4) and reacting the compound with a calcium compound to give pitavastatin calcium.

2. The production method according to claim 1, wherein the compound represented by the formula (1) used in (i) is obtained by
   (iv) reacting a compound represented by the following formula (6):

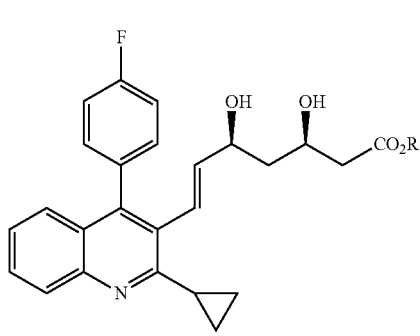

wherein R is a straight chain alkyl group having a carbon number of 1-8 or a branched alkyl group having a carbon number of 3-8, with an acid.

3. The production method according to claim 2, wherein the compound represented by the formula (6) used in (iv) is obtained by
   (v) condensing a compound represented by the following formula (7):

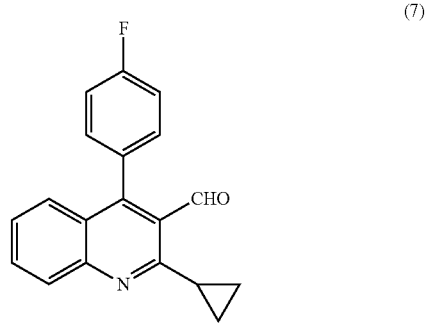 [SMILES: O=Cc1c(C2CC2)nc2ccccc2c1-c1ccc(F)cc1]

and a compound represented by the following formula (8):

wherein $R^5$ is a straight chain alkyl group having a carbon number of 1-8 or a branched alkyl group having a carbon number of 3-8 provided $R^5$ is different from R in said formula (1), in the presence of a base to give a compound represented by the following formula (9):

(9)

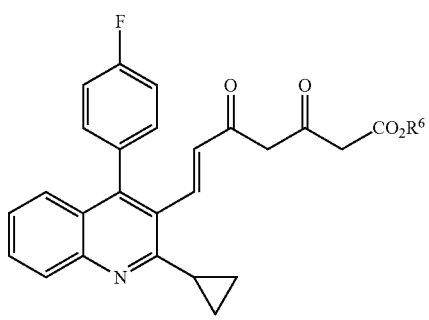

wherein R⁵ is as defined above;

(vi) reacting said compound represented by the formula (9) obtained in (v) with alcohol represented by R—OH wherein R is a straight chain alkyl group having a carbon number of 1-8 or a branched alkyl group having a carbon number of 3-8 to give a compound represented by the following formula (10):

(10)

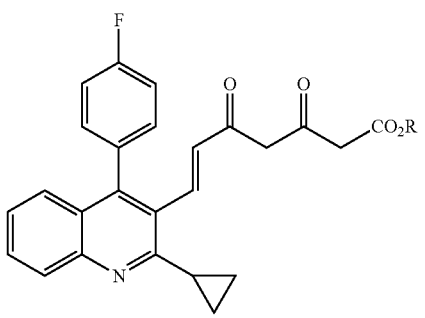

wherein R is as defined above; and (vii) reacting said compound represented by the formula (10) obtained in (vi) with an enzyme having an activity capable of stereoselectively reducing a carbonyl group, a microorganism or cell having an ability to produce the enzyme, a treated product of the microorganism or cell, and/or a culture solution containing the enzyme obtained by culturing the microorganism or cell.

4. The production method according to claim 2, wherein the compound represented by the formula (6) used in (iv) is obtained by (viii) reacting a compound represented by the following formula (12):

(12)

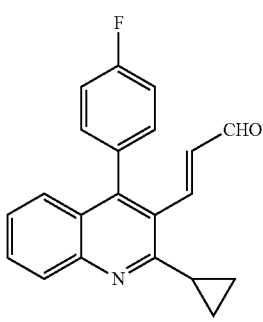

in the presence of a titanium catalyst with a compound represented by the following formula (13):

(13)

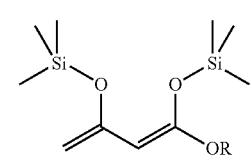

wherein R is a straight chain alkyl group having a carbon number of 1-8 or a branched alkyl group having a carbon number of 3-8, to give a compound represented by the following formula (14):

(14)

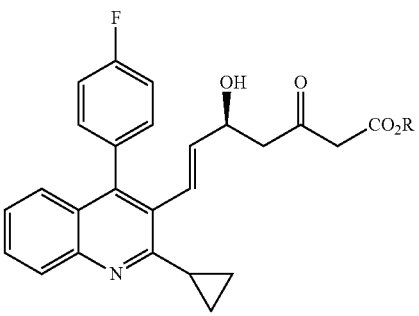

wherein R is as defined above; and (ix) reacting said compound represented by the formula (14) obtained in (viii) with an enzyme having an activity capable of stereoselectively reducing a carbonyl group, a microorganism or cell having an ability to produce the enzyme, a treated product of the microorganism or cell, and/or a culture solution containing the enzyme obtained by culturing the microorganism or cell.

* * * * *

UNITED STATES PATENT AND TRADEMARK OFFICE
CERTIFICATE OF CORRECTION

PATENT NO. : 10,676,441 B2
APPLICATION NO. : 15/749377
DATED : June 9, 2020
INVENTOR(S) : N. Watanabe et al.

Page 1 of 1

It is certified that error appears in the above-identified patent and that said Letters Patent is hereby corrected as shown below:

In the Claims

Column 59, Line 19 Claim 3, formula (9), change "$R^6$" to -- $R^5$ --.

Signed and Sealed this
Twentieth Day of October, 2020

Andrei Iancu
*Director of the United States Patent and Trademark Office*